United States Patent
Ganz et al.

(10) Patent No.: US 10,596,021 B2
(45) Date of Patent: Mar. 24, 2020

(54) OBESITY TREATMENT DEVICES, SYSTEMS, AND METHODS

(71) Applicants: Alexander S. Ganz, Minnetonka, MN (US); Robert A. Ganz, Minnetonka, MN (US)

(72) Inventors: Alexander S. Ganz, Minnetonka, MN (US); Robert A. Ganz, Minnetonka, MN (US)

(73) Assignee: Ganz Brake, LLC, Salt Lake City, UT (US)

( * ) Notice: Subject to any disclaimer, the term of this patent is extended or adjusted under 35 U.S.C. 154(b) by 46 days.

(21) Appl. No.: 15/853,793

(22) Filed: Dec. 23, 2017

(65) Prior Publication Data

US 2018/0177623 A1 Jun. 28, 2018

Related U.S. Application Data

(60) Provisional application No. 62/438,569, filed on Dec. 23, 2016, provisional application No. 62/526,007, filed on Jun. 28, 2017.

(51) Int. Cl.
*A61F 5/00* (2006.01)

(52) U.S. Cl.
CPC .................................. *A61F 5/0036* (2013.01)

(58) Field of Classification Search
CPC .. A61F 5/0036; A61F 2/04; A61F 5/00; A61F 5/0003; A61F 2002/045; A61F 5/0076; A61M 29/00
See application file for complete search history.

(56) References Cited

U.S. PATENT DOCUMENTS 6,149,581 A 11/2000 Klingenstein
6,675,809 B2 1/2004 Stack et al.
(Continued)

FOREIGN PATENT DOCUMENTS

CN 2699854 Y 5/2005
CN 2894655 Y 5/2007
(Continued)

OTHER PUBLICATIONS

Boccia, Gabriella, et al., Dyspeptic Symptoms in Children: The Result of a Constipation-Induced Cologastric Brake?, Clinical Gastroenterology and Hepatology, 2008, pp. 556-560, vol. 6, No. 5.
(Continued)

*Primary Examiner* — George J Ulsh
(74) *Attorney, Agent, or Firm* — Med Venture Management, LLC; Daniel C. Higgs

(57) ABSTRACT

Various devices, systems, and methods that can be used in the treatment of obesity and related illnesses are disclosed. In some instances, a portion of the bowel of an obese patient is distended for a therapeutically effective period. The distention may be achieved by introduction of an object that is of foreign origin relative to the body of the patient into the bowel of the patient. In some instances, the distention is achieved by a medical device that transitions from an undeployed state, in which the medical device is introduced into the bowel of the patient, to an expanded state in which the medical device distends the bowel by an amount sufficient to trigger an intestinal-gastric brake in the patient.

195 Claims, 29 Drawing Sheets

(56) References Cited

U.S. PATENT DOCUMENTS

| | | |
|---|---|---|
| 7,462,192 B2 | 12/2008 | Norton et al. |
| 7,476,256 B2 | 1/2009 | Meade et al. |
| 7,931,693 B2 | 4/2011 | Binmoeller |
| 8,075,582 B2 | 12/2011 | Lointier et al. |
| 8,100,932 B2 | 1/2012 | Nihalani |
| 8,147,561 B2 | 4/2012 | Binmoeller |
| 8,211,186 B2 | 7/2012 | Belhe et al. |
| 8,585,771 B2 | 11/2013 | Binmoeller et al. |
| 8,602,974 B2 | 12/2013 | Goldwasser et al. |
| 8,603,023 B2 | 12/2013 | Albrecht et al. |
| 8,628,554 B2 | 1/2014 | Sharma |
| 8,876,761 B2 | 11/2014 | Albrecht et al. |
| 9,456,916 B2 | 10/2016 | Connor |
| 9,526,648 B2 | 12/2016 | Sharma |
| 9,649,185 B2 | 5/2017 | Bangera et al. |
| 9,750,660 B2 | 9/2017 | Felder et al. |
| 9,895,103 B2 | 2/2018 | Hyde et al. |
| 10,183,154 B2 | 1/2019 | Hyde et al. |
| 10,299,857 B2 * | 5/2019 | Rajagopalan ...... A61B 18/1492 |
| 2002/0183853 A1 | 12/2002 | Mitchell et al. |
| 2003/0014127 A1 | 1/2003 | Talja et al. |
| 2005/0038415 A1 | 2/2005 | Rohr et al. |
| 2006/0058829 A1 | 3/2006 | Sampson et al. |
| 2006/0161139 A1 | 7/2006 | Levine et al. |
| 2007/0100367 A1 | 5/2007 | Quijano et al. |
| 2008/0065136 A1 | 3/2008 | Young |
| 2008/0161645 A1 | 7/2008 | Goldwasser et al. |
| 2008/0275445 A1 | 11/2008 | Kelly et al. |
| 2008/0312678 A1 | 12/2008 | Pasricha |
| 2009/0012469 A1 | 1/2009 | Nita |
| 2009/0192588 A1 | 7/2009 | Shin et al. |
| 2010/0105983 A1 | 4/2010 | Oneda et al. |
| 2010/0145301 A1 | 6/2010 | Magal |
| 2010/0324362 A1 | 12/2010 | Forsell |
| 2011/0196411 A1 | 8/2011 | Forsell |
| 2011/0295178 A1 | 12/2011 | Albrecht et al. |
| 2011/0295299 A1 | 12/2011 | Braithwaite et al. |
| 2013/0041424 A1 | 2/2013 | Neisz |
| 2013/0109912 A1 | 5/2013 | Binmoeller et al. |
| 2014/0114228 A1 | 4/2014 | Binmoeller et al. |
| 2014/0180188 A1 | 6/2014 | Chin et al. |
| 2014/0364959 A1 | 12/2014 | Attar et al. |
| 2016/0338865 A1 | 11/2016 | Campbell et al. |
| 2017/0172778 A1 | 6/2017 | Brister et al. |
| 2018/0092732 A1 | 4/2018 | Kringle et al. |
| 2019/0314181 A1 | 10/2019 | Ganz et al. |

FOREIGN PATENT DOCUMENTS

| | | |
|---|---|---|
| WO | 2012099610 A1 | 7/2012 |
| WO | 2015085010 A1 | 6/2015 |
| WO | 2018119477 A1 | 6/2018 |
| WO | 2020006279 A1 | 1/2020 |

OTHER PUBLICATIONS

Jackson, Daniel, Bowel Management Algorithm, 2007, available at https://pdfs.semanticscholar.org/dc36/59288d52bfce2babd268f804f009eb620983.pdf.

Jaffe, Tracy, et al., Large-Bowel Obstruction in the Adult: Classic Radiographic and CT Findings, Etiology, and Mimics, Radiology, Jun. 2015, pp. 651-663, vol. 275, No. 3.

Lee, Thomas, Leptos Biomedical to call it quits, MedCity News, Feb. 9, 2010, 2 pages, available at https://medcitynews.com/2010/02/leptos-biomedical-to-call-it-quits/.

Moon, Taegyun, et al., New Approach to Radial Expansive Force Measurement of Self Expandable Esophageal Metal Stents, ASAIO Journal, 2001, pp. 646-650.

Musial, F., et al., Effect of prolonged, continuous rectal distention on mouth-to-cecum and colonic transit time in pigs, Physiology and Behavior, 1992, p. 1021 (Abstract), vol. 52, No. 5.

Tjeerdsma, Hilda C., et al., Voluntary Suppression of Defecation Delays Gastric Emptying, Digestive Diseases and Sciences, May 1993, pp. 832-833, vol. 38, No. 5.

International Searching Agency, Search Report and Written Opinion of the ISA, International Application No. PCT/US2017/068378, dated Mar. 12, 2018, 19 pages.

International Searching Agency, Search Report and Written Opinion of the ISA, International Application No. PCT/US2019/039575, dated Oct. 17, 2019, 10 pages.

Cummings et al., Gastrointestinal regulation of food intake, The Journal of Clinical Investigation, Jan. 2, 2007, pp. 13-23, vol. 117, Issue 1.

* cited by examiner

OBESITY TREATMENT DEVICES, SYSTEMS, AND METHODS

RELATED APPLICATIONS

This application claims the benefit under 35 U.S.C. § 119(e) of U.S. Provisional Patent Application No. 62/438,569, titled Treatment of Obesity and Diabetes, filed on Dec. 23, 2016; and of U.S. Provisional Patent Application No. 62/526,007, titled Treatment of Obesity and Diabetes, filed on Jun. 28, 2017; the entire contents of each of which are hereby incorporated by reference herein.

BACKGROUND

Obesity is a common and important issue in the U.S. and worldwide that involves over 500 million obese people total. This number includes approximately 35-40% of adults in the U.S. with an associated cost of approximately $315 billion dollars for obesity-related diseases. At present, the global economic impact of obesity and related diseases approaches $2 trillion, much of that due to shortened lifespans, obesity associated comorbidities, and lost productivity. Among other diseases, obesity is directly related to heart disease and diabetes. Diabetes affects 382 million people worldwide, and up to 30 million adults in the U.S., with a U.S. cost of about $245 billion and an approximate worldwide cost of $600 billion per annum. Effective treatment of obesity in many cases can reverse diabetes and ameliorate heart disease, so effective treatment of obesity is an urgent medical need.

There are many medical, surgical, and device approaches to treating obesity, but none is ideal. There are at least 30 drugs on the market for obesity, but these have limited effects. There are at least five surgical procedures for weight loss, including, among others, Roux-en-Y gastric bypass, vertical sleeve gastrectomy, bilio-pancreatic diversion, gastric banding, and vagal nerve pacing. Surgery is effective, and multiple randomized, controlled trials have demonstrated profound weight loss (up to 60% at 5-year follow-ups), reduced mortality, and resolution of diabetes for the various surgical techniques. Surgery, however, is highly invasive, with associated mortality and morbidity, important pathophysiologic side-effects, and substantial cost. Major complications are common (up to 10%), including leaks, need for reoperation and revision, and malabsorption with multiple associated nutrient deficiencies are routinely seen. Most insurance companies do not routinely cover bariatric surgery, and most patients cannot afford the cost, so these procedures are underutilized.

There are also numerous endoscopic, and non-endoscopic, approaches to treating obesity, including endoscopic suturing devices (endoscopic sleeve gastrectomies), barrier/liner devices (GI dynamics, ValenTx), and devices that ablate duodenal mucosa (Fractyl). These approaches are safer and less invasive than surgery, but are not as efficacious as they yield more limited weight loss and are of only limited durability. Intragastric balloons (Obera, Reshape Medical etc.) for treating obesity also exist. These are solid balloons that are placed and inflated in the stomach to cause gastric distention and create a sense of fullness and satiety.

Embodiments disclosed herein address, resolve, ameliorate, and/or eliminate one or more of the disadvantages of known approaches for treating obesity and illnesses related thereto. For example, various methods, systems, and devices for treatment of obesity are achieved in less invasive manners, are more economical, are safer, and/or are more effective than one or more of the known approaches.

SUMMARY

Embodiments of devices, systems, and methods that can be used in the treatment of obesity and related illnesses are disclosed. In some embodiments, a portion of the bowel of an obese patient is distended for a therapeutically effective period. The distention may be achieved by introduction of an object that is of foreign origin relative to the body of the patient into the bowel of the patient. In some embodiments, the distention is achieved by a medical device that transitions from an undeployed state, in which the medical device is introduced into the bowel of the patient, to an expanded state in which the medical device distends the bowel by an amount sufficient to trigger an intestinal-gastric brake in the patient. Other embodiments are also disclosed.

DESCRIPTION OF FIGURES

The written disclosure herein describes illustrative embodiments that are non-limiting and non-exhaustive. Reference is made to certain of such illustrative embodiments that are depicted in the figures, in which.

DETAILED DESCRIPTION

Figure 1:
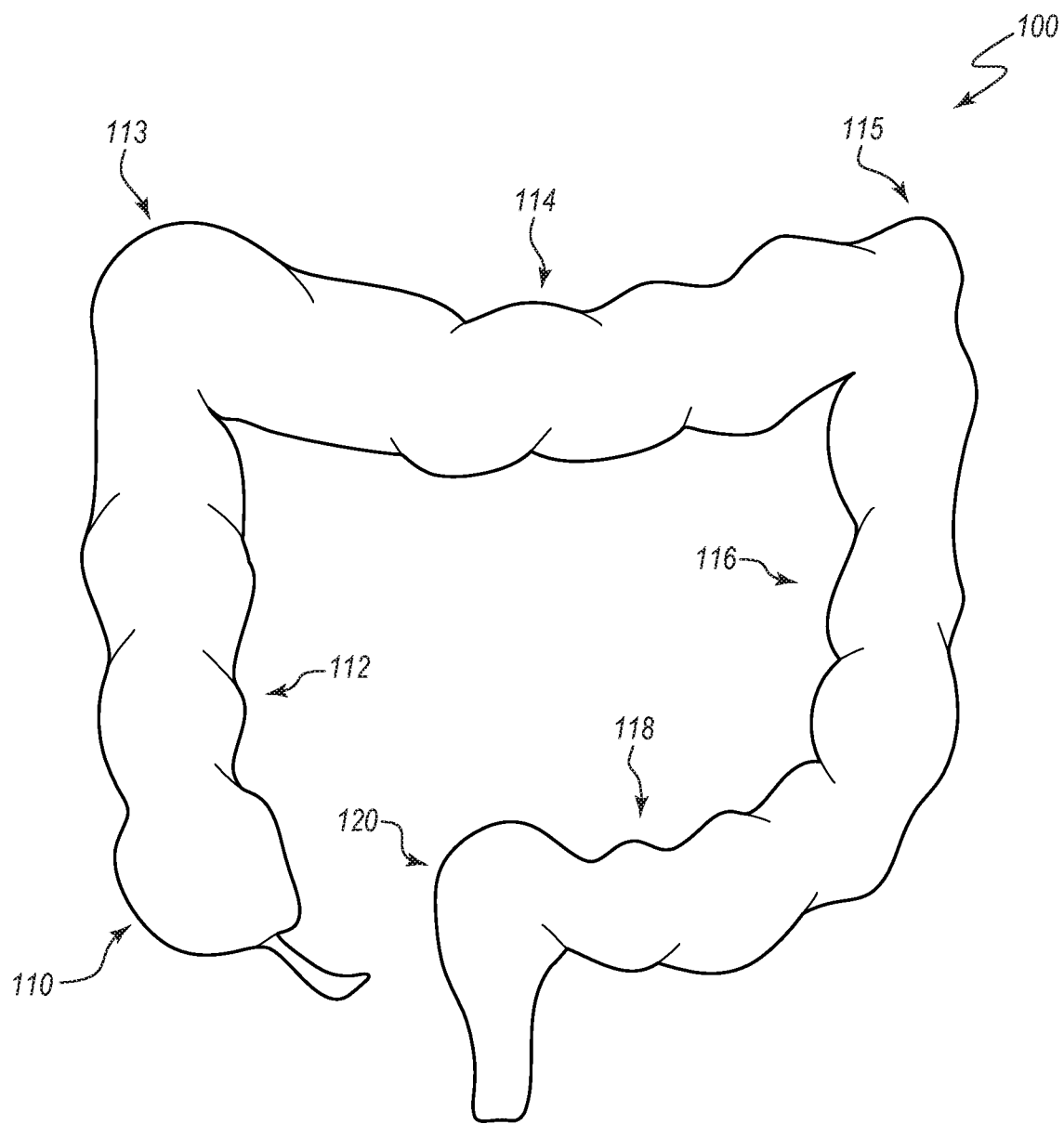
FIG. 1 is an elevation view of a colon in a natural or non-distended state.

Certain embodiments disclosed herein make advantageous use of a natural physiological response to distention of the bowel to treat obesity and illnesses related thereto. In particular, certain embodiments mimic the effects of bowel obstruction and bowel distention and/or to reproduce the normal physiological "intestinal-gastric brake," which is described further below. For example, certain embodiments artificially distend specific areas of the bowel (i.e., portions of the small or large intestines, such as the ileum, the cecum, the colon, the rectum, or any other portion of the luminal bowel) without causing an actual obstruction (or complete obstruction) of the bowel. Stated otherwise, various embodiments involve distention of a portion of the bowel to trigger an intestinal-gastric brake and/or a loss or reduction of appetite associated therewith, while permitting normal flow of material through the portion of the bowel that is distended.

Bowel obstructions of the colon or small intestine, that are either partial or complete, are poorly tolerated by humans (and other animals) and can cause loss of appetite (anorexia), nausea, and/or vomiting. This occurs because, with obstruction of any portion of the bowel (including obstruction of the bile ducts or pancreatic ducts), there can be both local distention of said organs and/or distention of the entire proximal bowel or portions of the more proximal bowel. Bowel distention in any part of the tubular gastrointestinal tract (small intestine, colon, etc.) drives chemical, hormonal, and neurological signaling that is the direct cause of the loss of appetite, nausea and vomiting, that occurs when any portion of the bowel is obstructed. Various gradations of symptoms can occur depending on exactly where the distention occurs, how distended the bowel becomes, and how rapidly the distention occurs.

Sometimes physiologic, non-obstructing distention of portions of the bowel that can occur as part of normal life can have effects similar to a bowel obstruction. As an example, when the colon in general, or, for example, the cecum (the most proximal portion of the colon) specifically, is distended during or following a meal as part of normal physiologic processes, appetite can be suppressed. Also, if a person has constipation, which can yield colon distention with stool, appetite can be suppressed. Or even during passage of stool following a large meal, such as with rectal distention, there can be suppression of appetite, and in rare cases, nausea or vomiting.

These effects are the normal physiologic response to colon, cecal, or rectal distention, which signals satiety to a person to prevent overeating. In part, this satiety signaling occurs because of the known "colo-gastric brake." The colo-gastric brake is a normal physiologic mechanism that slows or delays gastric emptying as the colon, cecum, or rectum distends. When this occurs, signals are sent to the brain and other parts of the gastrointestinal tract to both suppress appetite and decrease food intake, and also to delay gastric emptying which also suppresses appetite. As the cecum and/or more distal colon and rectum empty, the "brake" mechanism resolves, and stomach emptying and appetite return to normal. Similar braking can occur with cecal or rectal distention alone and/or distention of other portions of the colon or even small bowel. These braking effects are referred to generally herein as intestinal-gastric braking, or as an intestinal-gastric brake. The term intestinal-gastric brake includes the colo-gastric brake mechanism just described. Any device or method that can duplicate the intestinal-gastric brake can be an effective therapy for obesity and related diseases. In further instances, it can be particularly desirable to trigger the intestinal-gastric brake without—or without significantly, completely, or otherwise disadvantageously—obstructing the bowel. Certain embodiments disclosed herein thus achieve the advantages of intestinal-gastric braking for obesity treatment—such as, for example, appetite suppression—without triggering one or more of the disadvantageous effects of bowel obstruction.

Various embodiments disclosed herein differ significantly from intragastric balloons (from manufacturers like Obera, Reshape Medical etc.) that are used to treat obesity. Intragastric balloons are solid balloons, meaning that they do not define any openings or channels through which materials can pass, that are placed and inflated in the stomach to cause gastric distention and create a sense of fullness and satiety. It should be noted that use of such solid balloons is limited to placement in the stomach only. The stomach is a uniquely distensible, and uniquely J-shaped gastrointestinal organ that can accommodate a solid balloon or other structure without fear of obstruction.

Placement of a solid balloon in more tubular shaped parts of the gastrointestinal tract, such as the small bowel or colon, of a sufficient size to distend the bowel may not be possible since a solid balloon has a high likelihood of causing an emergency bowel obstruction outside of the stomach. It should also be noted that intragastric solid balloons are also not particularly efficacious for weight loss, since the great distensibility of the stomach allows patients to eat significant portions despite the presence of a balloon. Solid gastric balloons also have limited durability. They cannot be spontaneously passed into the more distal tubular bowel for fear of causing an emergency bowel obstruction, hence they need to be removed endoscopically.

Certain configurations and methods described herein can provide for safer and more efficacious non-surgical means to treat obesity that are minimally invasive and can readily and/or relatively cheaply be applied to the majority of obese subjects. These and/or other advantages of one or more embodiments will be apparent from the discussion herein. In some examples, a specific area of the tubular bowel is distended and/or partially filled to mimic certain of the effects of bowel obstruction and/or distention.

In certain embodiments, an object or structure is placed within the bowel of a patient so as to distend the bowel. Such distension can trigger the intestinal-gastric brake in the patient. The object or structure may include or define one or more passageways through which material can pass. In particular, the passageway(s) can be sufficiently large to permit passage therethrough of material that would otherwise pass through the portion of the bowel that is in distention (e.g., air, semiliquid, liquid, semisolid, or solid materials). The passageway(s) may permit such passage substantially without obstructing the natural passage of the material, and thus may cause distention of the bowel without obstructing the bowel.

In certain embodiments, the object or structure includes an expandable structure that is introduced into the bowel in an unexpanded state. The structure is expanded within the bowel to distend the bowel. When in the expanded state, the structure can define one or more passageways, which can be pathways through the device and/or between portions of the device that may include, or be in fluid communication with, one or more openings, perforations, channels, paths, etc. through which material can enter, pass through or by, and/or exit the structure. In some embodiments, the passageway is not entirely enclosed by the structure. Stated otherwise, the structure may define only a portion of the passageway, and may cooperate with the wall of the bowel to define a fully encircled or encompassed pathway through which material passes. The passageway(s) at least partially defined by the structure when in the expanded or deployed state allow gas, semiliquid, liquid, semisolid and/or solid material to pass through, thus avoiding actual obstruction of the bowel. In various embodiments, the structure may be secured to the bowel wall. For example, the structure may be placed in tension against the wall, may be anchored to the wall, may be adhered to the wall, etc. In other embodiments, the structure may be free floating within the bowel. The structure can be sized or otherwise configured to not migrate to more distal regions of the bowel. The structure can be applied to or reside in specific or designated areas of the bowel.

In some examples, the object or structure includes multiple components that are assembled within the bowel. For example, the structure may be formed of multiple filler components and/or one or more adhesives. The structure may be assembled within the bowel, such as by adhering filler components to the bowel lining and/or to each other. As more and more filler and/or adhesive is applied, the bowel wall can be distended to a variable degree. In some instances, an adhesive can include a mucosal adhesive that can adhere, or partially adhere, to the inner lining of the bowel and/or may additionally adhere filler components to each other. In other or further instances, an adhesive may be used to adhere the filler components to each other. For example, in some instances, the components are adhered only to each other without adhering to the bowel. Accordingly, the structure may comprise a conglomerate of the filler components, and the conglomerate can be adhered directly to the lining of the bowel or, in other instances, the conglomerate can be freely mobile in the lumen of the bowel, but within a limited length of the bowel. For example, rather than being adhered to the bowel, the conglomerate can be free floating within the bowel. The conglomerate can be sized or otherwise configured to not migrate to more distal regions of the bowel. The conglomerate structures can be applied to or reside in specific or designated areas of the bowel.

FIG. 1 depicts a large intestine or colon 100 in a natural state. The colon 100 includes multiple sections. The most proximal section of the colon 100 is the cecum 110, which receives material from the small intestine (specifically, the ileum). Distal to the cecum 110 is the right or ascending colon 112, the hepatic flexure 113, the transverse colon 114, the splenic flexure 115, the left or descending colon 116, the sigmoid colon 118, and the rectum 120. Stool material or chyme that passes through the colon 100 is substantially in liquid or semiliquid form within the cecum 110 and the ascending colon 112, and progressively solidifies along more distal tracts of the colon 100.

Figure 2:
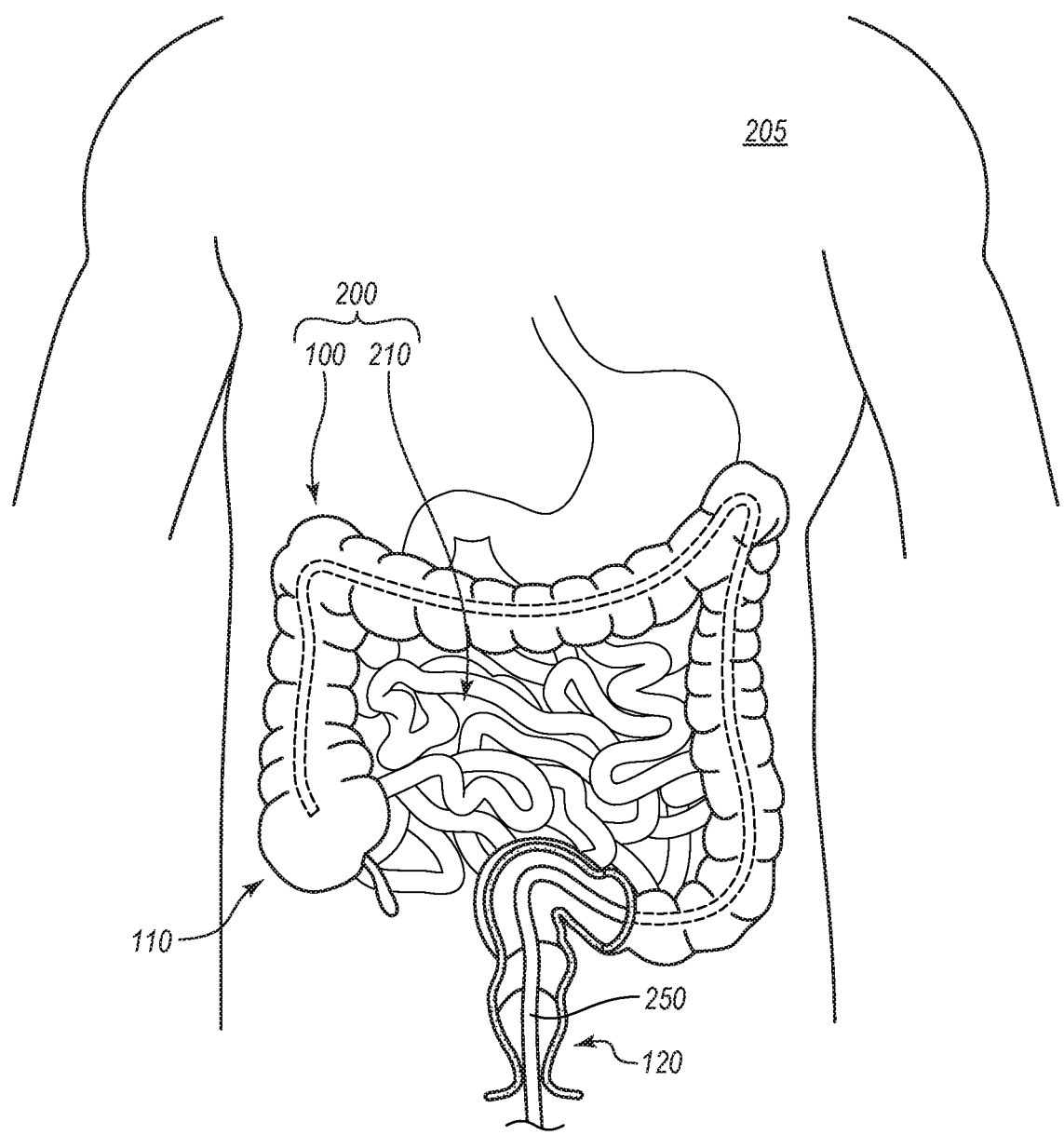
FIG. 2 is a cutaway elevation view of a patient showing the bowel of the patient, wherein a stage of an illustrative method for treating obesity of the patient in which an endoscope has been advanced to the cecum of the patient is depicted.

FIG. 2 depicts the bowel 200 of a patient 205. The bowel 200 includes the small intestine 210 and the colon 100.

Figure 3:
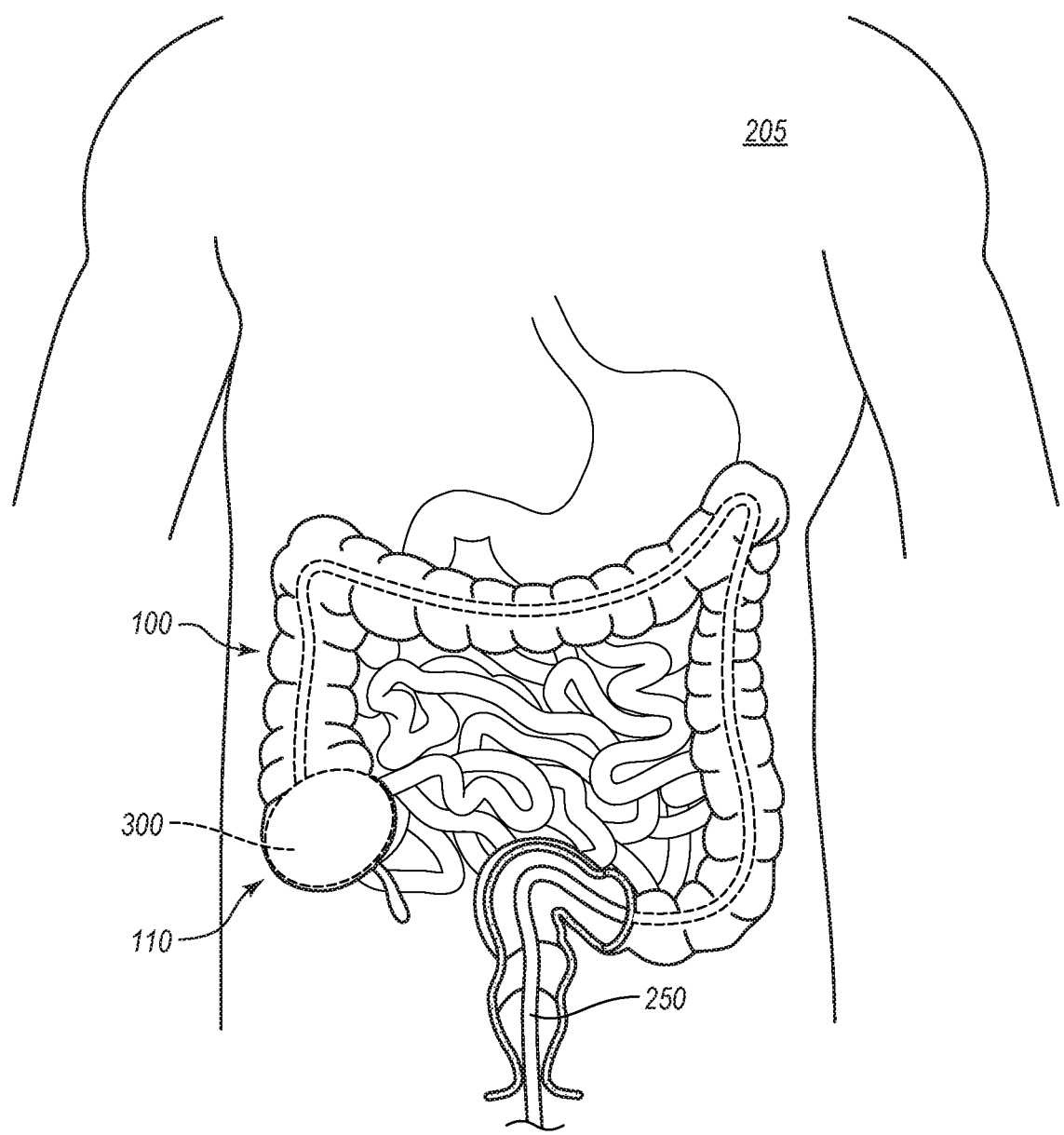
FIG. 3 is another cutaway elevation view of the patient such as that of FIG. 2 showing another stage of the method in which a structure has been implanted in the cecum of the patient.

FIGS. 2 and 3 depict separate stages of a method for treating obesity of the patient 205. The patient 205 may be suffering not only from obesity, but potentially from other diseases or illnesses caused by, tied to, or otherwise related to obesity. For example, amelioration or resolution of the underlying obesity condition could ameliorate or resolve one or more other conditions of the patient 205. Accordingly, although the method may be termed as a method for treating the obesity of the patient 205, the method may simultaneously also be a method for treating one or more of the other conditions of the patient 205 (diabetes mellitus, steatohepatitis, etc.). For example, the method of treating obesity of the patient 205 may likewise or alternatively be termed as a method of treating diabetes mellitus, a method of treating steatohepatitis, and/or a method of treating some other condition that is treatable by treating the underlying obesity of the patient.

As shown in FIG. 3, the illustrated method includes the placement of a medical device 300, which may also or alternatively be referred to herein as a structure or object 300, which is of foreign origin relative to the patient 205, within the bowel 200. The term "of foreign origin relative to the patient" is used herein to describe items, whether naturally occurring or synthetic, that originate externally from the patient. Thus, the objects or structures may themselves be naturally occurring items (for example, nutrients; bacteria; natural filler materials, such as natural fibers; etc.) or artificial items (for example, non-naturally occurring or synthetic materials, such as synthetic fibers; stents, balloons, or cages formed of synthetic materials; etc.), but the items originate external to the patient 205. For example, stool that might distend a portion of the bowel is not an object of foreign origin relative to the patient 205, due to the generation thereof within the patient, whereas a medical device that is introduced into the bowel 200 for distention in any suitable manner is an object of foreign origin relative to the patient.

The object 300 can be introduced into a specified region of the patient 205 by non-natural mechanisms. In such instances, the mechanisms are separate from physiological processes that are naturally conducted by the body (e.g., material transport through the digestive tract), and may be achieved or controlled by a medical practitioner. For example, placement of the object 300 within the bowel 200 may be achieved via an endoscope, catheter, guidewire, and/or other device that has been advanced into the bowel by a medical practitioner. Other placement methods or mechanisms are also possible.

With reference again to FIG. 2, in the illustrated method, an endoscope 250 is introduced through the rectum 120 of the patient 205 and advanced proximally through the bowel 200 into the cecum 110. Accordingly, the endoscope 250 may, specifically, be a colonoscope, and may be advanced to the cecum 110 in manners typically employed in colonoscopy procedures. The endoscope 250 may include an internal lumen or instrument channel (see FIG. 5A, lumen 262), which may also be referred to as a tool channel, via which the object 300 can be introduced into the cecum 110.

With reference again to FIG. 3, the structure 300 is shown within the cecum 110 after having been advanced through the instrument channel of the endoscope 250 and assembled, expanded, and/or otherwise oriented within the cecum 110 so as to distend the cecum 110. The structure 300 distends the cecum 110 sufficiently to trigger the intestinal-gastric brake in the patient 205. Moreover, the structure 300 may permit passage of material through the cecum 110, such as in manners discussed below. For example, the structure 300 may define one or more passageways through which material passes. Specifically, the one or more passageways permit passage therethrough of material that would otherwise pass through the cecum, in the absence of the structure 300. Accordingly, the structure 300 can distend the cecum 110 without obstructing the natural flow or passage of material through the cecum 110. The structure 300 thus may trigger physiological responses to distention, without triggering one or more physiological responses that might otherwise accompany such distention due to an obstruction of the bowel lumen.

After placement, or implantation, the structure 300 is then left in the cecum 110 while distending the cecum 110. In some instances, the distention may be partial. For example, in some instance, the structure 300 may contact or press against, and thus expand, only a portion of a periphery of the cecum 110. In other instances, the distension may be complete. For example, the structure 300 may contact or press against, and thus expand, an entire periphery of the cecum 110 (e.g., may contact and expand an entire inner circumference of the cecum 110).

In some instances, the distention may be continuous. For example, the structure 300 may distend the cecum 110 by a constant amount, which amount may be sufficient to retain the cecum 110 in the expanded orientation independent of conditions that would otherwise cause natural fluctuations in the size of the cecum 110 over time. By way of illustration, in some embodiments, the structure 300 is or includes an expandable stent which, when expanded, is placed in tension against an inner wall of the bowel 200. Once expanded, the stent can maintain a substantially constant size and configuration, and may maintain the cecum 110 in a substantially constant distended state. The stent may distend the cecum 110 by a sufficient amount such that if the cecum 110 encounters natural conditions that would cause the cecum 110 to expand, in the absence of the stent, the cecum 110 nevertheless does not expand due to the already enlarged configuration imparted to it by the stent.

In other or further instances, the structure 300 may intermittently distend the cecum 110, such as by permitting fluctuations in the size (e.g., a diameter) of the cecum 110. For example, the structure 300 may distend the cecum 110 to a minimum distended state, but may permit the cecum 110 to fluctuate naturally to larger distended states when particularly distending conditions arise in the cecum 110. In certain of such instances, the structure 300 is secured to the wall of the cecum 110 so as to fluctuate in size in tandem with the cecum 110. For example, in certain embodiments, the structure 300 comprises a stent that is configured to define a minimum expanded size (e.g., minimum diameter), but can expand beyond the minimum size to larger sizes. The stent may, for example, be a self-expanding stent that generally presses against the cecum 110 to achieve a state of equilibrium, at which the cecum 110 is distended. When the cecum 110 expands beyond this distended state due to natural conditions within the cecum 110, the stent may likewise increase in size due to its resilient bias against the cecum 110 (e.g., tensioned against the cecum 110). In some embodiments, the stent may fluctuate in size by any amount, whereas in other embodiments, the stent may be delimited to fluctuate to no greater than a maximum size (e.g., maximum diameter).

In other instances, in which the structure 300 intermittently distends the cecum 110, the structure 300 is not secured to the wall or lining of the cecum 110 in a manner that would cause the structure 300 to fluctuate in size. For example, the structure 300 may define a substantially constant size and may be free floating within the cecum 110. By way of illustration, in some embodiments, the structure 300 comprises a stent, ball, cage, or other structure that is expandable to a fixed size. After the structure 300 has been expanded in the cecum 110 to this fixed size to distend the cecum 110, the structure 300 may remain substantially fixed relative to the cecum 110 under normal conditions, such as due to frictional interference between an outer surface of the structure 300 and the lining of the cecum 110. However, when particularly distending conditions arise in the cecum 110, the cecum 110 may distend to a size greater than that caused by the expanded structure 300. As the structure 300 is not fixedly secured to the cecum 110, the structure 300 may be free to float within the cecum 110 and make intermittent contact therewith. The structure 300 thus may rotate, bounce around, or otherwise move within the cecum 110. The structure 300 may be desirably sized and/or otherwise configured (e.g., provided with a tapered end or tapered ends) that can prevent the structure 300 from migrating from the cecum 110 to more distal portions of the colon 100 under such circumstances. In some instances, at least some portion of the structure 300 substantially always remains in contact with the cecum 110, even during such periods of further enlargement of the cecum 110.

In view of the foregoing, the structure 300 may continuously and/or intermittently trigger the intestinal-gastric brake. This can reduce an appetite of the patient 205 and/or otherwise reduce a food intake of the patient 205. Over time, the reduced food intake of the patient 205 can result in weight loss for the patient. The structure 300 can remain within the bowel 200 of the patient 205 for a therapeutically effective period.

As used herein the term "therapeutically effective period" denotes a period of time over which a therapeutically significant weight loss is achieved for the patient 205. Thus, the period may be therapeutically effective in the treatment of the obesity and/or one or more related diseases due to the weight reduction of the patient 205 achieved during its duration. In various instances, the therapeutically effective period is an amount of time sufficient to achieve a total weight loss of the patient 205 of no less than 5, 10, 15, 20, or 25 percent. In other or further instances, the therapeutically effective period is an amount of time sufficient to achieve an excess weight loss of no less than 10, 15, 20, 25, 30, 40, or 50 percent. As used herein, the term "excess weight loss" refers to a reduction of excess weight, the excess weight being calculated as a difference between the patient's actual body weight at the time the structure 300 is first introduced into the patient 205 and a target healthy weight of the patient. The target healthy weight of the patient can be determined in any suitable manner. For example, the target healthy weight can be calculated to be the weight necessary to achieve a body mass index (BMI) of 24.9 (i.e., the maximum BMI to be within the normal weight range). In other or further instances, the therapeutically effective period is no less than 1, 3, 6, 9, or 12 months.

As previously noted, the structure 300 can be configured to distend the cecum 110 by an amount sufficient to trigger the colo-gastric brake. For example, in various instances, the structure 300 can be configured to distend the cecum 110 relative to a relaxed or natural configuration by no less than 20, 30, 40, 50, 60, 75, or 100 percent. In adult patients, the cecum is generally approximately 6 centimeters in length (typically no shorter than about 1.5 centimeters and no longer than about 8 centimeters) and is generally about 6.5 centimeters in diameter (typically no smaller than about 1.5 centimeters and no larger than about 9 centimeters). Accordingly, there can be a significant variation in the size of the cecum 110 from one patient to another. In various embodiments, the structure 300, when distending the cecum 110, can define an outer or maximum diameter within a range of from about 6 centimeters to about 10 centimeters, or that is no less than about 6, about 7, about 8, or about 10 centimeters.

Distention of the cecum 110 can be achieved relative to a healthy state of the cecum 110. Stated otherwise, the structure 300 can be sized or otherwise configured to distend the cecum 110 relative to a normal size of the cecum 110. The purpose of the structure 300 may not, in various instances, be to expand the cecum 110 so as to return it from an abnormally small condition (e.g., due to cancer or other disease) to normal dimensions, but rather, to distend the cecum 110 from a natural size to an enlarged size to trigger the colo-gastric brake.

The structure 300 can be eliminated from the cecum 110 and/or, more generally, from the body of the patient 205 in a variety of manners. In some embodiments, as further discussed below, the structure 300 can be configured to break down within the body of the patient 205 over time. For example, the structure 300 can include a bioresorbable material that degrades over time. The structure 300 may degrade sufficiently such that it no longer distends the cecum 110, and may pass spontaneously or naturally through the remaining portion of the colon 100 and out of the patient 205. In may be desirable for degradation to the point of discontinued distention and/or natural expulsion of the structure 300 from the patient 205 to occur at some point in time after completion of the therapeutically effective period discussed above. In other or further instances, after completion of the therapeutically effective period, the structure 300 may be actively retrieved from the patient 205. For example, a colonoscopy procedure may be performed to retrieve the structure 300 from the patient 205. In certain instances, standard retrieval techniques may be used, such as by the use of a snare or other device deployed from the colonoscope.

Although the foregoing discussion has focused on implanting the structure 300 in the cecum 110, the discussion likewise applies to implantation of the structure 300, or similar structures, within other or further portions of the bowel 200. For example, in various embodiments, one or more structures may be implanted in the ascending colon 112, the hepatic flexure 113, the transverse colon 114, the splenic flexure 115, the left or descending colon 116, the sigmoid colon 118, and/or the rectum 120. In other or further embodiments, one or more structures may be implanted in the small intestine 210, such as, for example, in the ileum. Such implantations can similarly trigger intestinal-gastric brakes, and may do so without yielding a bowel obstruction. This pattern of disclosure applies equally to other embodiments described herein. That is, although many embodiments are disclosed herein in the context of implantations in the cecum, the disclosures can likewise apply to implantations in other portions of the bowel (mutatis mutandis, to the extent applicable).

In some instances, it may be advantageous to implant one or more structures 300 in the cecum 110 and/or the ascending colon 112. In these regions of the bowel 200, material that naturally passes through the intestinal tract (e.g., stool or chyme) is substantially liquid or semiliquid. Accordingly, passageways defined by the one or more structures 300 can readily pass the material therethrough. Moreover, distention of the bowel in these sections generally will not give rise to an urge in the patient 205 to defecate, as might occur in more distal portions of the colon. Furthermore, in some instances, positioning device or devices within the cecum 110 and/or the ascending colon 112 can reduce any likelihood of an unintended bowel obstruction, such as in situations where the devices degrade over time and are permitted to pass naturally through the bowel. The cecum 110 and the ascending colon 112 are distal to the ileocecal valve, at which such degraded devices, or pieces of such degraded devices, could get caught and give rise to an obstruction.

A wide variety of configurations are contemplated for the structure 300. Illustrative examples of such structures are depicted in FIGS. 4-20 and are discussed in the written descriptions associated with these drawings.

Figure 4:
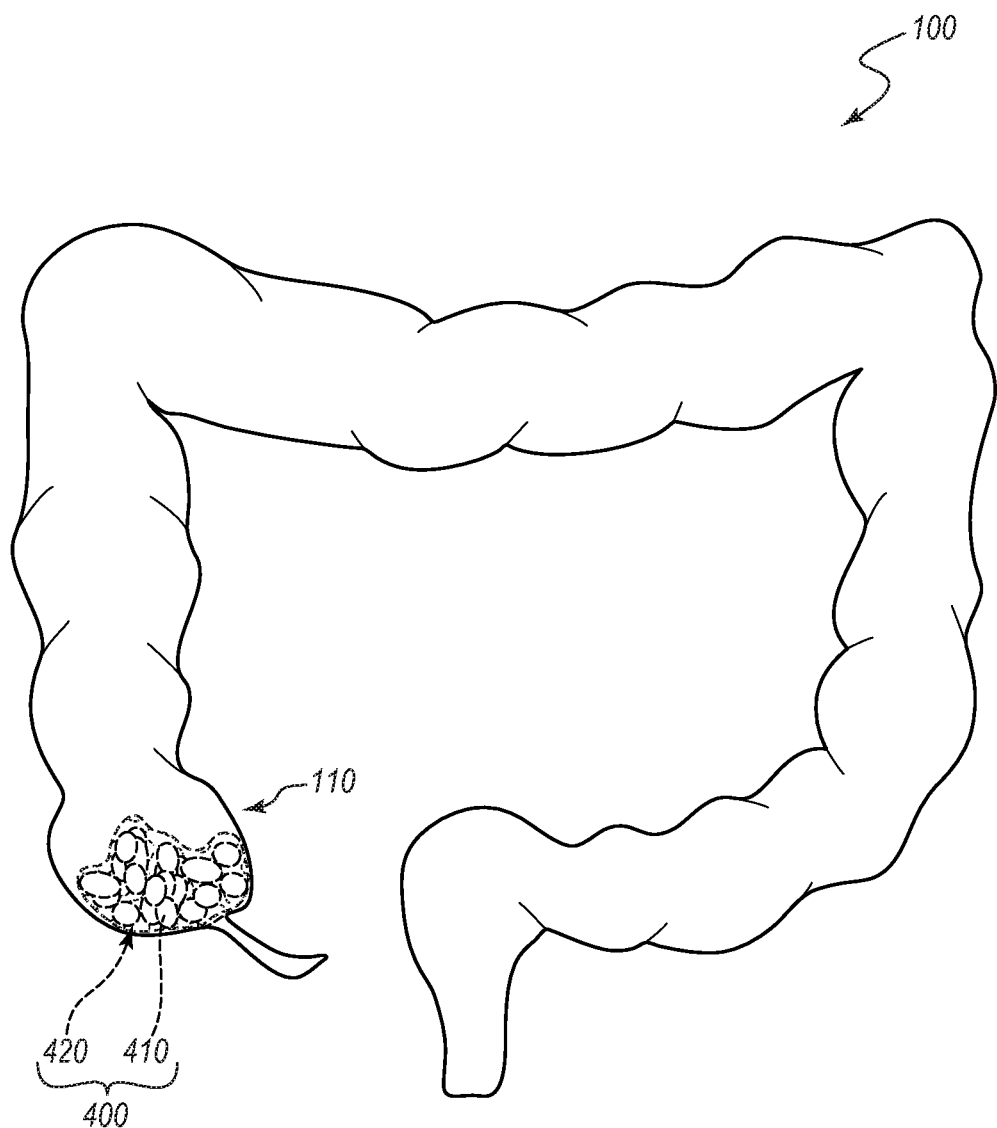
FIG. 4 is another elevation view of the colon similar to that of FIG. 1, but depicting a stage of another illustrative method in which a structure that has been introduced into the cecum of a patient to distend the cecum.

FIG. 4 depicts a stage in another method of treating obesity of the patient 205, in which a medical device, object, or structure 400, has been implanted in the cecum 110 of the patient 205. In particular, the structure 400 is formed of a plurality of individual components or particles 410 that have been introduced into the cecum 110. The particles 410 can be assembled within the cecum 110 to form a conglomerate structure, which can partially fill the cecum 110. The particles 410 can be adhered—e.g., via one or more adhesives 420—to the lining of the cecum 110 and/or each other, and in various embodiments, the resultant conglomerate structure 400 can be adhered to the lining, can otherwise be secured to the lining (e.g., may be tensioned against the lining upon formation of a structure with sufficient rigidity to press against the bowel wall), or can be unattached relative to the lining and free floating within the cecum 110.

In certain embodiments where the structure 400 is freely movable within the colon 100, a first amount of adhesive 420 can be applied to the lining, and then further adhesive 420 can be added thereto. The additional adhesive thus can adhere to adhesive material already initially applied in the lumen of the bowel, creating, in essence, a large ball or mass of glue or slime which sticks to itself, but not to the wall of the bowel. The initial adhesive application can cure quickly, preventing attachment to the wall, and then additional adhesive can be applied to the initial adhesive amount. Curing can be of variable time periods. In some instances, the structure 400 may be formed entirely of one or more adhesives.

In some embodiments, the adhesive is further combined in various amounts with various amounts of one or more of fiber (e.g., soluble or insoluble fibers of any type), cellulose, hemicellulose, lignans, mucilages, beta-glucans, pectin, guar, polydextrose, starches, dextrins, inulins, *psyllium*, bran, and/or any other type of natural or artificial fiber or other filler, to create a ball or mass shape of any suitable size, thereby distending the lumen of the bowel to any suitable size or diameter. The relative amounts of adhesive versus filler material can vary. For example, in various embodiments, the structure 400 includes 100% adhesive, a majority of adhesive, a minority of adhesive, 100% filler material, a majority of filler material, a minority of filler material, or relatively equal amounts of adhesive and filler material. As previously noted, the final conglomerate structure 400, which may assume a ball shape or other suitable shape, can be adherent to the wall or non-adherent to the wall of the bowel.

The conglomerate structure 400 can also be degradable over variable periods of time. The adhesive can degrade over a variable period of time, slowly dissolving or degrading, and either be absorbable or pass out of the bowel, naturally like stool. As the adhesive degrades, variable amounts of filler material are released and pass out of the bowel, similar to stool, thus gradually decreasing the size of the conglomerate structure and gradually reducing the distention effect.

Thus, the effects of bowel distention achieved by the conglomerate structure 400 can be reversible over a variable period of time, depending on the degradation characteristics of the adhesive and/or filler material. This can be the case whether the conglomerate structure 400 is adherent or nonadherent to the wall.

The conglomerate structure 400 can be positioned in place via adhesion to a variety of different portions of the bowel and, further, at a variety of different locations on the wall of the bowel. The conglomerate structure 400 can be attached and/or formed in a variety of different configurations. For example, the structure 400 can be formed as a series of layers, may be substantially spherical (e.g., ball-shaped), can define an annulus (e.g., circumferentially applied to the wall to ultimately distend the wall about a full periphery thereof), can define a portion of an annulus (e.g., hemi-circumferentially applied), and/or may define other fully or partially obstructing configurations. In some instances, a non-adherent and freely movable structure 400 may stay in place due to virtue of its size. For example, the structure 400 may define a ball shape of a diameter that is larger than the diameter of the bowel lumen, and may define one or more passages through which material can pass through the bowel. In further instances, due to naturally occurring constricted regions (e.g., regions of reduced diameter) along the bowel tract, the large diameter of the structure 400 prevents the structure 400 from migrating distally through the bowel. Accordingly, the structure 400 may not be permitted to pass through the distal regions of the bowel and out of the patient 205 until the structure 400 has degraded by a sufficient amount. In some instances, the substantially ball-shaped structure 400 may be formed with one or more passageways therethrough to permit passage of material therethrough prior to such degradation and spontaneous passage (e.g., defecation) of the structure 400, or portions thereof.

Specific adhesives that can be applied to the wall of the bowel include various materials known in the field of tissue adhesives, such as polyethylene glycols, polyethylene glycol copolymers, triglycerides, diglycerides, esters, fatty alcohol esters, polyacids, polyamines, gelatins, chitosans, polyactive esters, isocyonates, anhydrides, cyanoacrylates, methylmethacrolyates, cross-linking adhesives, other tissue adhesives. In other or further instances, the adhesives can include materials such as those that bind dentures to teeth, mollusk glues, etc. The adhesives may be used in any suitable combination, cured in any of a variety of manners (e.g., as are known in the art), used with or without added enzymes or preservatives, used with or without added salts, and/or be partially or completely degradable, etc. The adhesives may be used in any suitable amount and may yield any desired orientation and/or configuration.

In some embodiments, the conglomerate structure 400 can contain one or more varieties of antibiotics and/or anti-microbial material (such as copper or silver) that can have delayed release, which can favorably impact the surrounding microbiome. In some embodiments, the conglomerate structure 400 includes one or more of any of a variety of drugs that can affect the microbiome and/or that can directly treat obesity and/or diabetes.

In some embodiments, the conglomerate structure 400 is attached to native bowel wall mucosa. In other embodiments, the mucosa of the bowel wall is purposely damaged or ablated with radio-frequency energy, heat, cryotherapy, or other forms of electromagnetic radiation in order to damage, remove and/or fibrose the mucosa. In some instances, the structure 400 can better attach to the bowel wall where such ablation has been performed, either by adhering to new fibrotic tissue, or by adhering to deeper layers of the bowel wall, such as the submucosa or deeper muscle layers, or both. In some instances, such an ablation technique can also be used to sterilize the bowel wall underneath the adhesive.

With reference again to FIG. 4, in the illustrated method, a colonoscope (e.g., such as the endoscope 250 depicted in FIGS. 2 and 3) is advanced into the cecum 110. Thereafter, adhesive 420 and/or filler material 410 is injected through an injectable catheter placed through the biopsy port (i.e., the tool channel) in the endoscope, or may be injected directly through the endoscope. In other instances, rather than injecting the adhesive 420 and/or the filler material 410, some other form of application is employed (brushing, spraying, etc.). In other instances, the adhesive and/or the filler material is instead advanced into the cecum 110 alongside the endoscope, such as via a channel through a removable or disposable covering over the endoscope. In some methods, one or more adhesives are first applied to the wall of the cecum 110. Thereafter, one or more particles 410 are applied to the adhesive 410. In still other embodiments, the one or more particles 410 and the adhesive 420 may be combined (e.g., prior to advancement through the endoscope or within the endoscope) and then applied to the wall of the cecum 110, or otherwise introduced into the cecum 110, via the endoscope. The processes may be repeated until a conglomerate structure 400 of a desired configuration is achieved. The conglomerate structure 400 can distend at least a portion of the cecum 410 in an amount sufficient to trigger a colo-gastric brake.

As previously discussed, in various embodiments, the conglomerate structure 400 can adhere to the mucosa (inner lining) or deeper layers of the cecum 410, such as the submucosal or muscle layers, or fill between the spaces of the bowel wall layers, and fill the bowel wall and/or lumen thus distending said portion to a diameter of a desired size. As more adhesive and/or filler material is applied, the new material could adhere to the previous material and pile up in a mass or ball of material of various size and shape, but all to the effect of distending the lumen or wall of said bowel.

In other embodiments, an implantable object for distending the bowel can be an expandable structure that is delivered to the desired location within the bowel. The structure can be delivered in an undeployed (e.g., reduced profile, unexpanded, partially expanded) state and can be deployed at the desired location to an expanded state. Any of a variety of such structures are contemplated. For example, in various embodiments, an expandable medical device can comprise a stent, a cage, a ball, a balloon, or other similar mechanism. In various embodiments, the structure can define one or more passageways (e.g., openings, perforations, channels, pathways, or the like) that allow materials (e.g., gasses, semiliquids, liquids, semisolids, and/or solids) to pass through the structure. In some embodiments, the structure can be freely movable (e.g., free floating) in the lumen of the bowel, but may include features that prevent migration (e.g., distal migration) through the bowel. In other embodiments, the structure is at least temporarily or intermittently secured to the bowel wall or inner lining of the bowel. In various embodiments, the structure can fill, or partially fill, the lumen of the bowel, and may distend the bowel by a designated, predetermined, or desired amount. A variety of configurations are contemplated, of which a few illustrative examples are discussed hereafter.

FIGS. 5A-5D depict various stages of an illustrative method of implanting or deploying a medical device 500 (FIGS. 5C and 5D) in the colon 100 of the patient 205. The medical device 500 may also or alternatively be referred to herein as a distention device, distention object, expandable structure, implant, etc. In the illustrated embodiment, the device 500 is an expandable stent, and in particular, is a balloon-expandable stent. Accordingly, the device 500 may alternatively be referred to herein as the stent 500.

Figure 5A:
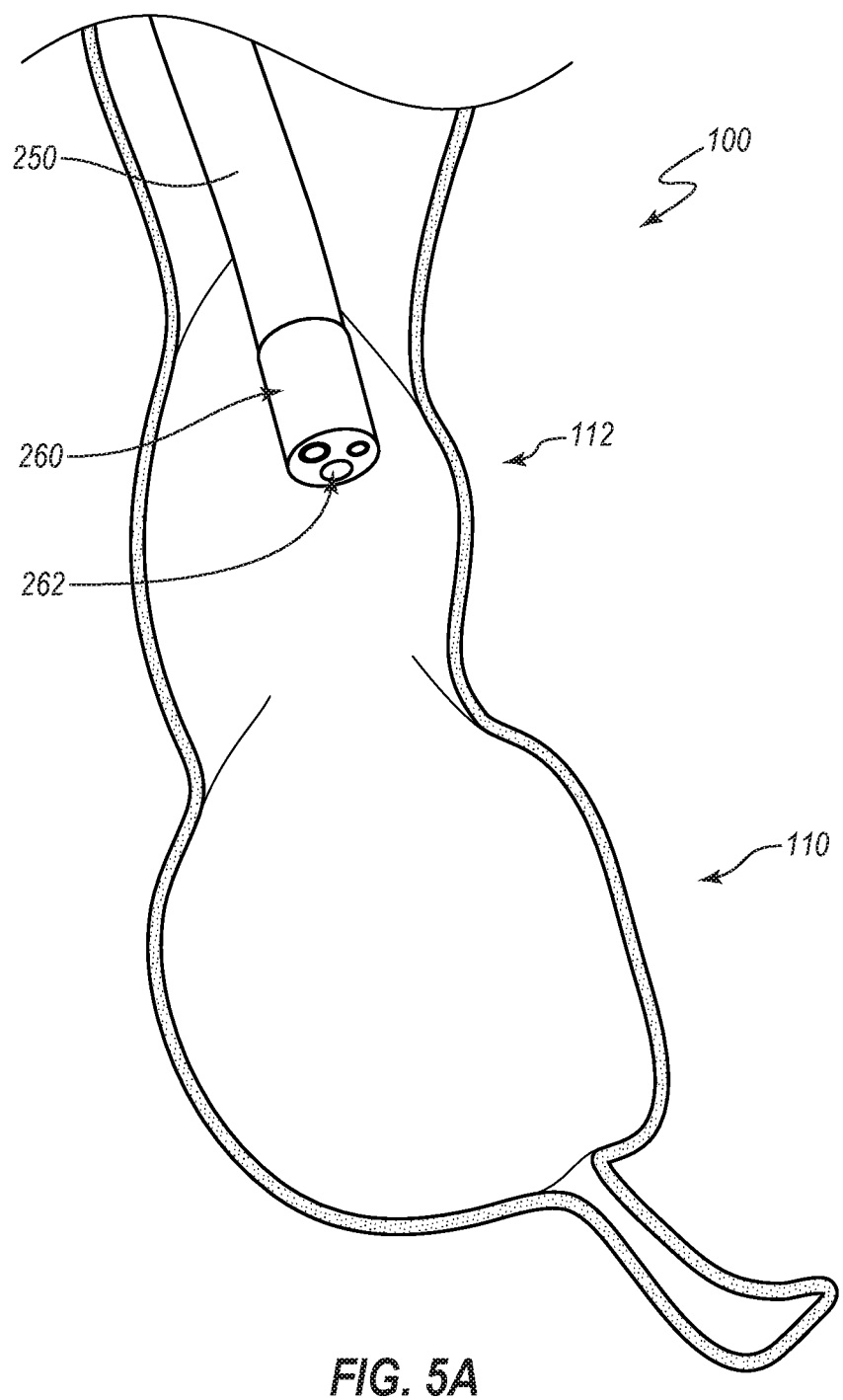
FIG. 5A is a cross-sectional view of a portion of the colon of a patient during another illustrative method in which an endoscope, shown in perspective, is being advanced toward the cecum of the patient.

With reference to FIG. 5A, in an early stage of the method, an endoscope 250 is inserted into the colon 100 in the same manner as depicted in FIG. 2. In particular, as shown in FIG. 2, the endoscope 250 is introduced through the rectum 120 of the patient 205 and is advanced proximally through the lumen of the colon 100. A longitudinal axis of the endoscope 250 can be aligned with, parallel to, or may otherwise track or follow a longitudinal axis of the lumen of the colon. FIG. 5A depicts a tip 260 of the endoscope 250 at a proximal end of the ascending colon 112 and nearing the cecum 110. Unless otherwise specified herein, the terms "proximal" and "distal" refer to the direction of passage of material through the gastrointestinal tract of the patient 205. Thus, the patient's mouth is at the proximal end of the gastrointestinal tract and the rectum is at the distal end of the gastrointestinal tract. The endoscope 250 includes a lumen 262, which may be referred to as a tool channel, an instrument channel, or simply as a channel.

Figure 5B:
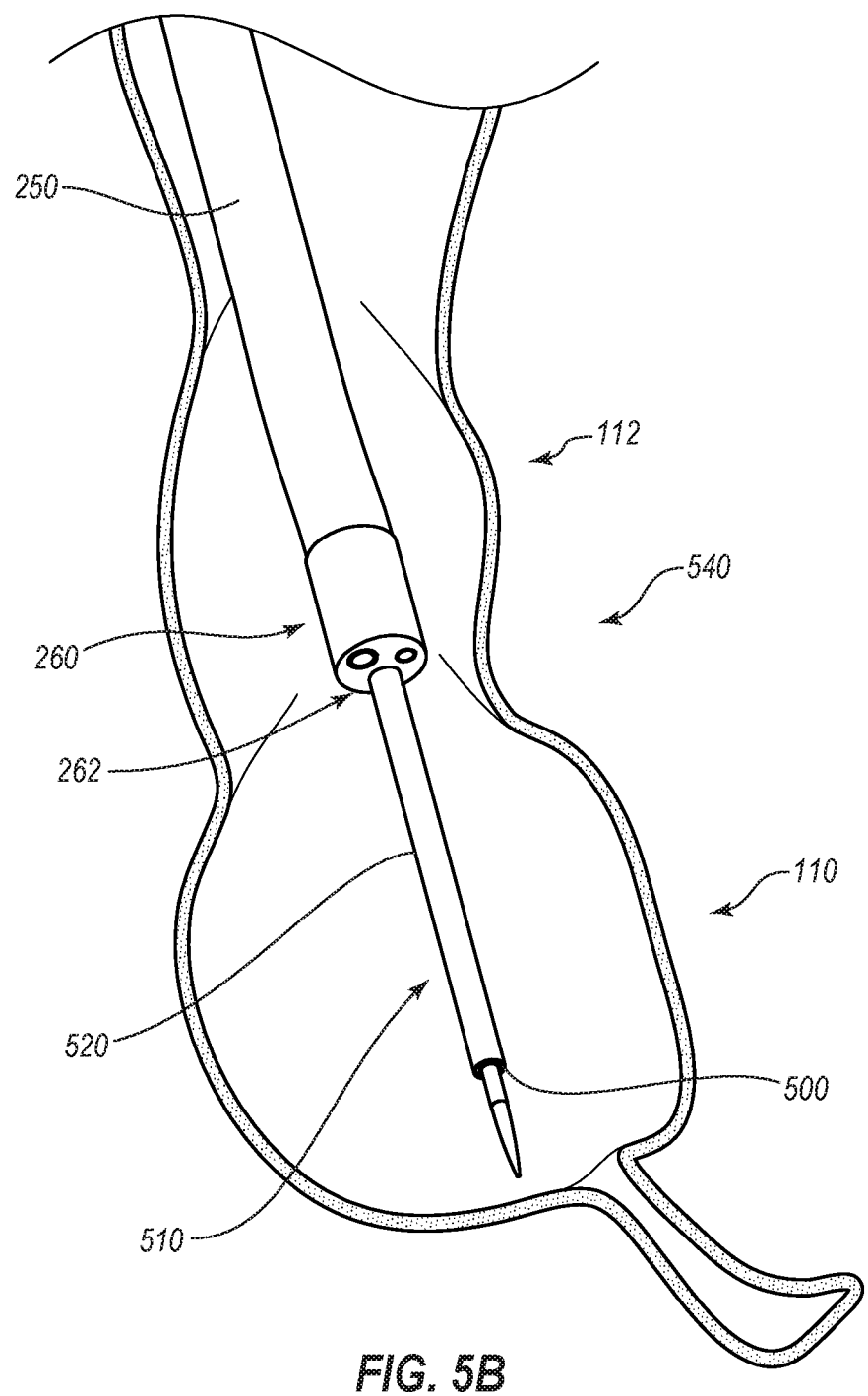
FIG. 5B depicts another stage of the method in which a catheter is advanced out of a distal end of the endoscope into the cecum.

FIG. 5B depicts a later stage of the method at which the endoscope 250 has been advanced slightly further toward the cecum 110 and held in place. A catheter 510 to which the stent 500 is coupled is then inserted proximally through the lumen 262 of the endoscope 250 so as to position the stent 500 within the cecum 110. In the illustrated embodiment, the stent 500 is covered with a protective sleeve 520. In some methods, the sleeve 520 is removed from the stent 500 and retracted through the endoscope 250 prior to deployment of the stent 500. For example, the sleeve 520 may retracted via a wire to which it is attached or via any other suitable mechanism. In some embodiments, the stent 500 is self-expandable, such that removal of the sleeve 520 permits the stent 500 to expand outwardly into contact with the walls of the cecum 110 and distend the cecum 110 to an expanded diameter. In other embodiments, such as that presently illustrated, the stent 500 is not self-expanding. In other or further embodiments, a sleeve 520 is not used.

The endoscope 250, the catheter 510, and the stent 500 may be referred to as a system 540 for treating obesity (or associated illnesses). The system 540, or some or all of the components thereof, may also or alternatively be referred to as a medical device deployment system for distending a portion of the bowel.

Figure 5C:
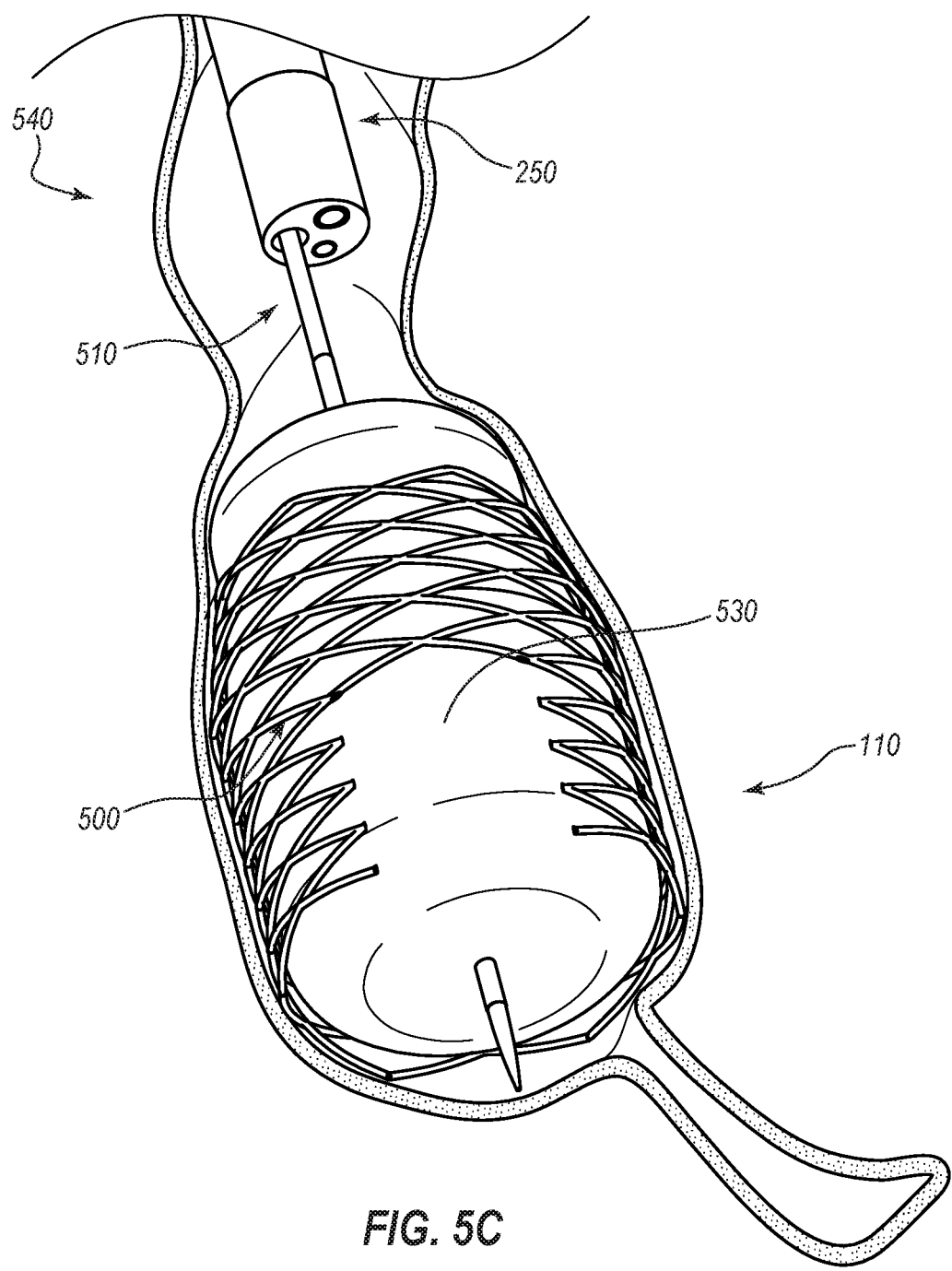
FIG. 5C depicts another stage of the method in which a stent is being deployed into contact with the cecum via the catheter.

FIG. 5C depicts a later stage of the illustrative method after which the sleeve 520 has been removed. At the moment depicted in this drawing, a balloon 530 that is coupled to the catheter 510, and over which stent 500 has been positioned, is inflated via the catheter 510. For example, a proximal end of the catheter (i.e., the end that remains external to the patient 205) may be coupled with an inflation syringe (not shown) or other suitable inflation device, and fluid may be delivered from the inflation syringe, through a lumen of the catheter 510, and into the balloon 530 to expand the balloon 530 and thereby expand the stent 500. As used herein, the term "fluid" is used in its ordinary sense and includes materials that have no fixed shape, yield easily to external pressure, or are flowable, such as gases (e.g., air, nitrogen, etc.) and liquids (e.g., saline, deionized water, etc.).

Figure 5D:
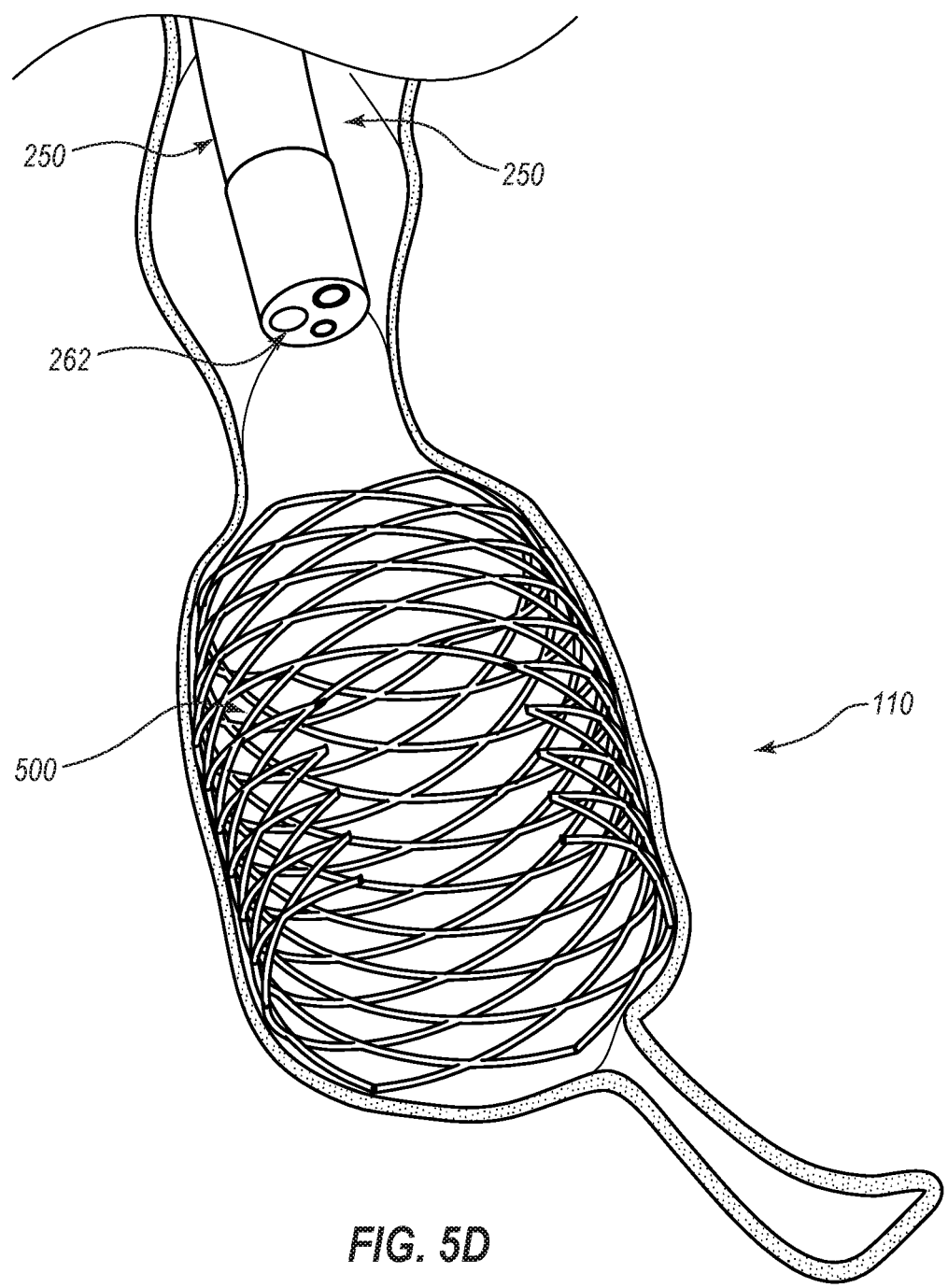
FIG. 5D depicts another stage of the method in which the stent has been deployed and the catheter has been retracted relative to the endoscope.

FIG. 5D depicts yet a later stage of the illustrative method after which the balloon 530 has been deflated (e.g., via retraction of the inflation fluid), and the catheter 510 has been at least partially withdrawn through the lumen 262 of the endoscope 250. After complete or partial withdrawal of the catheter 510, the endoscope 250 (and, in some instances, the catheter 510 if still positioned within the lumen 262) is withdrawn from the patient 205.

Figure 5E:
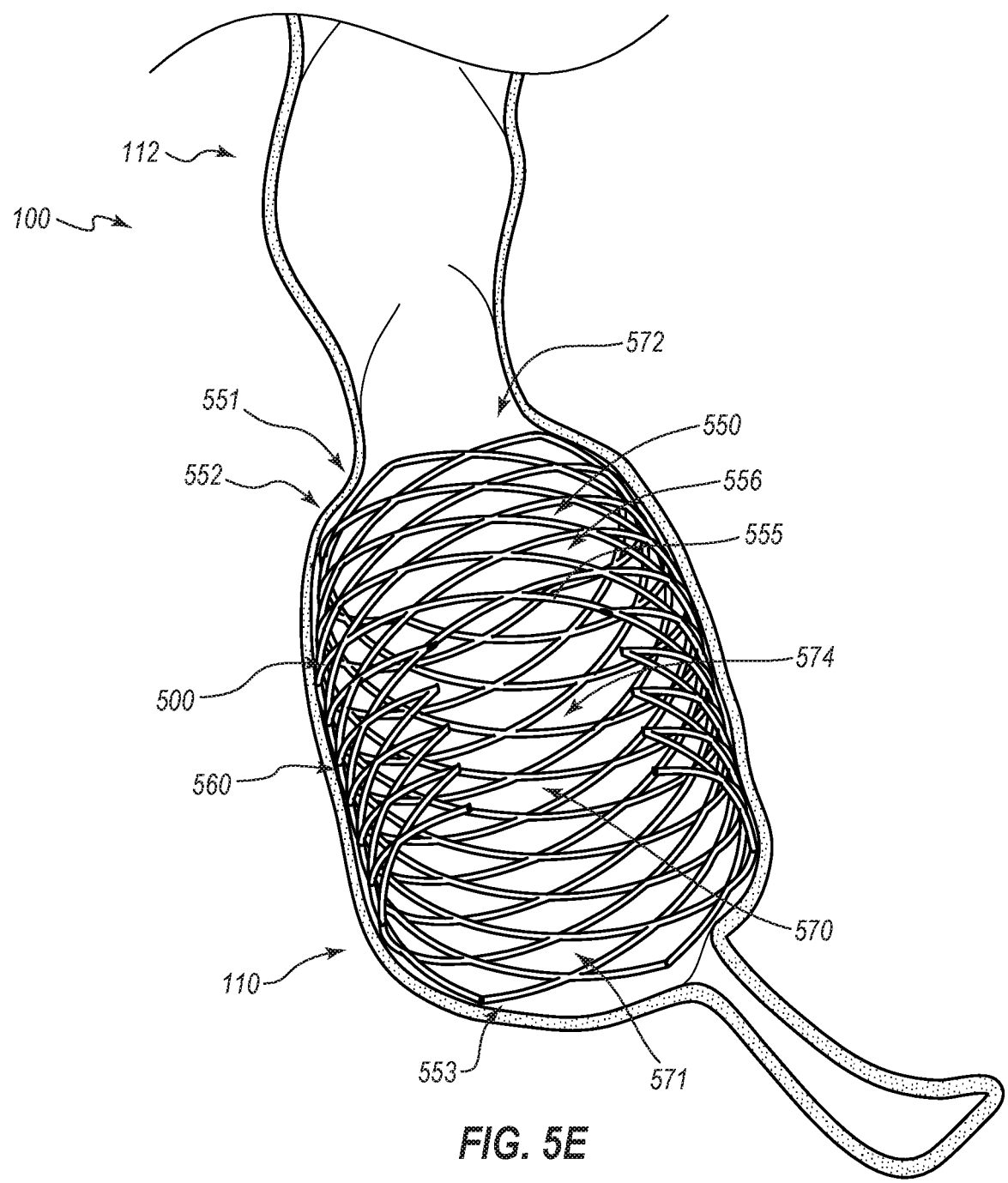
FIG. 5E depicts another stage of the method in which the stent is implanted in the cecum and the endoscope has been retracted from the patient.

FIG. 5E depicts a later stage of the illustrative method after the endoscope 250 has been withdrawn from the patient 205. The stent 500 remains in its expanded configuration and continues to distend the wall of the cecum 110. As previously discussed, the stent 500 can continuously or intermittently distend the cecum 110 by an amount sufficient to trigger an intestinal-gastric brake of the patient 205, which can suppress an appetite of the patient. The stent 500 can remain implanted in the patient 205 for a therapeutically effective period over which a weight of the patient is reduced by a desired amount.

In various embodiments, the stent 500 may include any of the dimensions or other features discussed above with respect to the device 300. For example, in various embodiments, an outer or maximum diameter of the stent 500 is within a range of from about 6 centimeters to about 10 centimeters, or that is no less than about 6, about 7, about 8, or about 10 centimeters. Indeed, the stent 500 is an example of the device 300 described above, and thus may exhibit some or all of the properties described above with respect thereto. As a further example, the illustrated embodiment of the stent 500 defines a substantially constant configuration, or stated otherwise, is not susceptible to fluctuations due to varying physiological conditions experienced within the cecum 110, as might be experienced by more resiliently flexible stents. Various embodiments of the stent 500 thus may achieve continuous distention of the cecum 110 or intermittent distention of the cecum 110, depending on a magnitude of the distention encountered by the cecum 110 (e.g., percentage increase in size) and/or the severity of the physiological conditions encountered within the cecum 110 over the course of implantation.

In the illustrated embodiment, the stent 500 is tensioned against the wall of the cecum 110 to achieve distention thereof. The stent 500 thus may be secured to the wall of the cecum 110, although, in other or further embodiments, the stent 500 may nevertheless be free floating within the cecum 110. The term "free floating" does not necessarily or solely connote a complete lack of contact with the wall of the cecum 110, although such may be the case on at least some occasions (such as if the cecum 110 expands beyond the distended configuration imparted thereto by the stent 500). Rather, this term also includes situations where the stent 500 contacts only a portion of a periphery of the wall and/or only a portion of a periphery of the stent 500 contacts the wall, such as may occur as the stent 500 moves around in the cecum 110. In some embodiments, the stent 500 may be attached to the wall more securely or more permanently, so as to be less susceptible to movement (e.g., rotation) within the cecum 110. For example, one or more anchoring protrusions (e.g., hooks or spikes—not shown) may extend outwardly from a frame or body 550 of the stent 500 and may embed in the wall of the cecum 110. In other or further instances, the stent 500 may be adhered to the wall of the cecum 110, such as, for example, via any of the adhesive previously described herein.

Whether or not the stent 500 is anchored or otherwise securely fastened to the wall of the cecum 110, in various embodiments, the stent 500 can include features that inhibit or prevent migration (or premature migration, in the case of stents 500 that are configured to eventually pass through the bowel and out of the patient 205) to more distal regions of the colon 100. For example, in the illustrated embodiment, the stent 500 generally defines a bulbous shape that is similar to, although enlarged relative to, a natural bulbous shape of the cecum 110. In the illustrated embodiment, a distal end 551 includes a taper 552 by which a diameter of the stent 500 is reduced in the distal direction. This taper 552 can assist in maintaining the stent 500 pointed in the distal direction. In particular, the narrowing of the stent 500 in the distal direction can assist in pointing the stent 500 in the same direction that the colon 100 narrows, which is likewise in the distal direction. Moreover, at least one of the maximum and minimum diameters of the stent 500 may be sufficiently large to prevent the stent 500 from migrating distally, given that the cecum 110 defines a larger diameter than does at least an immediately adjacent portion of the ascending colon 112. Further, in some embodiments, the taper 552 of the distal end, which may serve to center or embed the distal end 551 of the stent 500 at a distal end of the cecum 110, and/or a length of the stent 500, which may exceed a diameter of the stent 500 in some embodiments, can prevent or inhibit rotation of the stent 500 about axes perpendicular to a longitudinal axis of the stent 500 (which can be substantially aligned with a longitudinal axis of the cecum 110).

In other or further embodiments, the stent 500 may include a similar taper at a proximal end 553 thereof. Such a taper may allow the stent 500 to more closely conform to the natural bulbous shape of the cecum 110.

The body 550 of the illustrated stent 500 includes a substantially cylindrical region 560 that extends along a majority of its length, and is capped by a more conical, parabolic, or rounded shape defined by the taper 552, as previously discussed. The body 550 can be formed in any suitable manner. In the illustrated embodiment, the body 550 comprises a plurality of wires, struts, connectors, or support members 555, which in the illustrated embodiment cross each other at consistent angles and extend along regularly spaced paths or intervals. The widths of the support members 555 are relatively small, such that the support members 555 define a plurality of large openings 556.

The body 550 is substantially hollow, in that it defines a large primary channel or passageway 570. Each of the openings 556 defined by the support members 555 is in fluid communication with the passageway 570, and thus each opening 556 defines an entrance to or exit from the passageway 570. Moreover, the body 550 defines a proximal opening 571 at an entry to and a distal opening 572 at an exit of the passageway 570.

The passageway 570 may be sufficiently large to permit passage of material therethrough without substantially impeding the flow of the material. Stated otherwise, the body 550 of the stent can effectively distend the wall of the cecum 110 while the passageway 570 defined by the body 550 can permit substantially unimpeded or unobstructed flow of the material through the body 550. Due to the thinness of the struts 555 and the expanded lumen size provided by the stent 500, in some embodiments, the presence of the stent 550 can actually expand the flow capacity of the cecum 110. In various other embodiments, the stent 550 reduces the flow capacity of the cecum 110 by no greater than 5, 10, 15, 20, 25, 30, 40, or 50 percent. In other or further embodiments, the stent 500 obstructs no greater than 5 percent of material from passing through the cecum 110.

In the illustrated embodiment, a sidewall region defines a notch 574, which extends the proximal opening 571 longitudinally. In some embodiments, the notch 574 can be aligned with the ileocecal valve upon implantation of the stent 500. Flow material from the ilium thus may pass through or by the notch 574 and into the stent 500. The stent 500 thus may provide even less impedance to material flow into the cecum 110. In other embodiments, the notch 574 may be absent, and in further embodiments, this absence may have little overall effect on flow of material into the passageway 570 due to the size and number of the openings 556.

In various embodiments, the stent 500 may comprise braided filament, such as wire or other material, or may be laser cut from a material. Any suitable material is contemplated, including, for example, metals, shape-memory alloys (e.g., Nitinol), polymers, etc. The stents 500 can be made of any suitable shape and oriented as needed to interface with the anatomy of the patient 205. For example, other embodiments that may be implanted at other regions of the bowel may be shaped differently than the illustrated stent 500. In some embodiments, the stent 500 can be self-expanding. For example, in some embodiments the stent 500 may be formed of a heat-setting or elastomeric material.

In some embodiments, the stent 500 can be drug- and/or nutrient-eluting. Stated otherwise, the stent 500 can comprise an eluting material that includes one or more drugs, nutrients, hormones, peptides, neurotransmitters, bacteria, and/or other substances that can be released over time. The substances may be appetite suppressants of any suitable variety and/or may otherwise be useful or therapeutic in the treatment of obesity and/or related illnesses. In some embodiments, the stent 500 may be formed with a metallic scaffold and an elutable substance (drug, nutrient, or otherwise) can be dispersed in a polymer matrix, which may conformally surround the scaffold. The polymers may be primarily biostable to bind the substance to the stent and modulate the elution of the substance into the bowel.

In various embodiments, substances that the stent 500 can elute over time can include peptides, such as cholecystokinin (CCK) for stents 500 configured for implantation in the upper or small intestine, or glucagon-like peptide-1 (GLP1) and/or oxyntomodulin for stents 500 configured for implantation in the lower intestine or colon.

In other or further embodiments, the stent 500, or portions thereof, may be formed of a biodegradable or bioresorbable material of any suitable variety. In some embodiments, the as the material of which the stent 500 is formed biodegrades or is bioresorbed over time, the structural integrity of the material weakens. Accordingly, whereas the stent 500 may initially have sufficient structural rigidity to press against the wall of the bowel to distend the bowel, the stent 500 may eventually weaken to where it is no longer able to distend the bowel. Ultimately, the stent 500 may reduce in size to be spontaneously passed through the bowel and out of the patient 205. For example, in some instances, the stent 500 may weaken and/or may break down into multiple separate pieces that may each be sufficiently small to naturally or spontaneously pass through the bowel. In various embodiments, the stent 500 could last a predetermined amount of time in the applied position (e.g., days, weeks, months, or years). In some instances, the stent 500 is configured to ensure that bioresortpion proceeds to the point of terminating distention only after a therapeutically effective period has passed from the time of implantation.

In some embodiments, the stent 500 is configured to be retrievable, such as via an additional colonoscopy procedure. For example, in various embodiments, the stent 500 can have features that permit a medical practitioner to grab it, collapse it, and retrieve it, such as, for example, via any suitable snaring device and/or a reduced diameter cover into which the snaring device may draw the stent 500.

Figure 6:
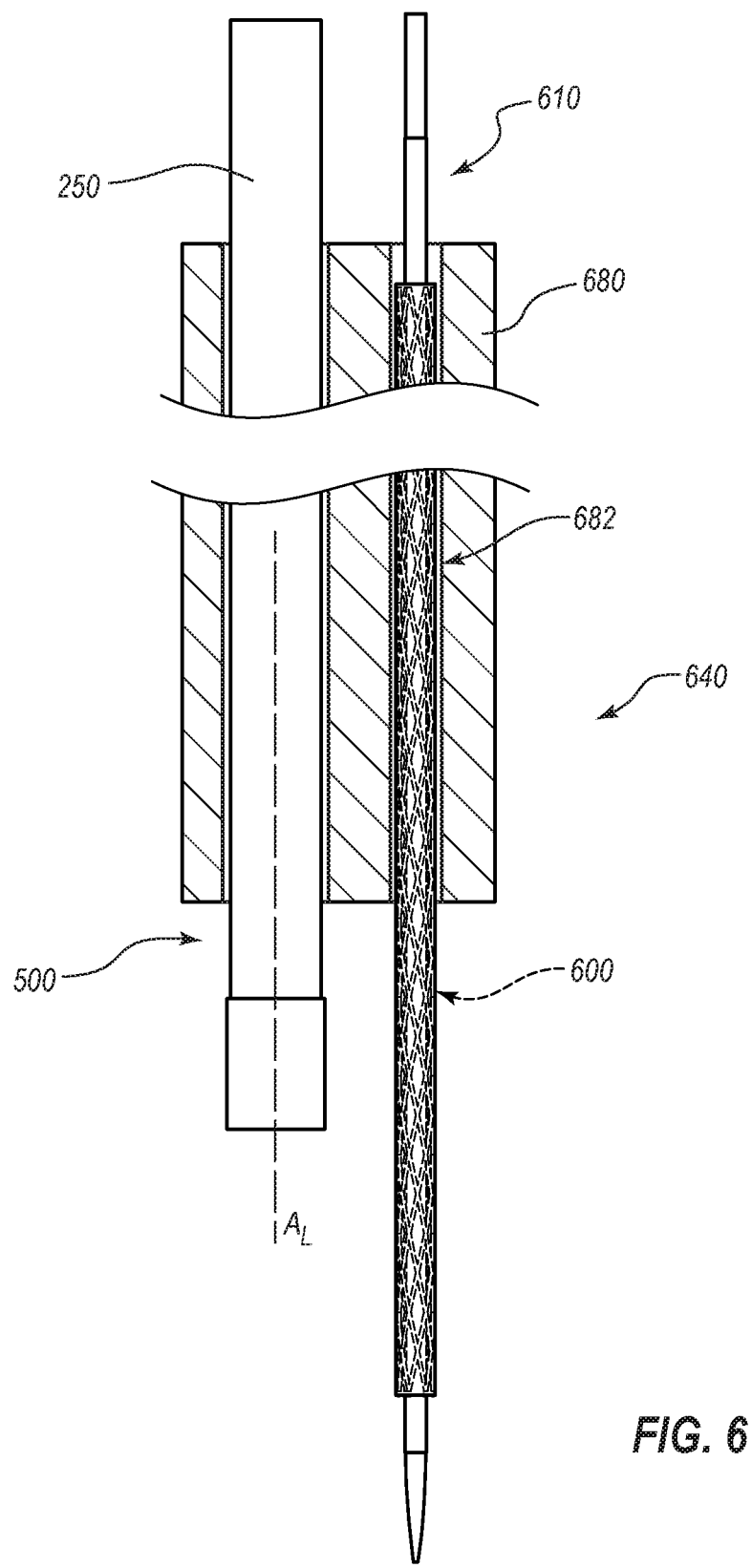
FIG. 6 is a cross sectional view of an embodiment of a system that can be used to implant an embodiment of an expandable medical device within the bowel of a patient.

FIG. 6 depicts another system 640 that can resemble the system 540 described above in certain respects. Accordingly, like features are designated with like reference numerals, with the leading digits incremented to "6." Relevant disclosure set forth above regarding similarly identified features thus may not be repeated hereafter. Moreover, specific features of the system 640 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 640. Any suitable combination of the features and variations of the same described with respect to the system 540 can be employed with the system 640, and vice versa. The same is also true of a stent 600 that is deployable via the system 640 and the stent 500 of the system 540. That is, disclosures regarding various medical devices can be appropriately applied to other, similarly numbered medical devices herein, in the interest of streamlining the present discussion. This pattern of disclosure applies equally to further embodiments depicted in subsequent figures and described hereafter, wherein the leading digits may be further incremented.

The system 640 can include the endoscope 250 discussed above (which can comprise any suitable endoscope, such as any suitable variety of colonoscope), and can further include a covering 680 or attachment for the endoscope, and a balloon catheter 610 to which a stent 600 is coupled. The system 640 can be used to implant the stent 600 in a patient 205 in manners such as those discussed above. However, rather than inserting a catheter 610 through a lumen of the endoscope 250, the catheter 610 is instead inserted through a lumen 682 defined by the attachment or covering 680. In various embodiments, the covering 680 may be selectively attachable to and/or detachable from the endoscope 250, and may be disposable. The lumen 682 may be substantially parallel to the instrument channel of the endoscope 250, and likewise may be substantially parallel to a longitudinal axis $A_L$. In various embodiments, a longitudinal axis of the instrument channel of the endoscope 250 may be colinear or aligned with the longitudinal axis $A_L$, or may run parallel thereto. Accordingly, in the illustrated embodiment, the stent 600 may be introduced into the patient 205 alongside (e.g., exterior to an outer surface of) the endoscope 250.

Figure 7A:
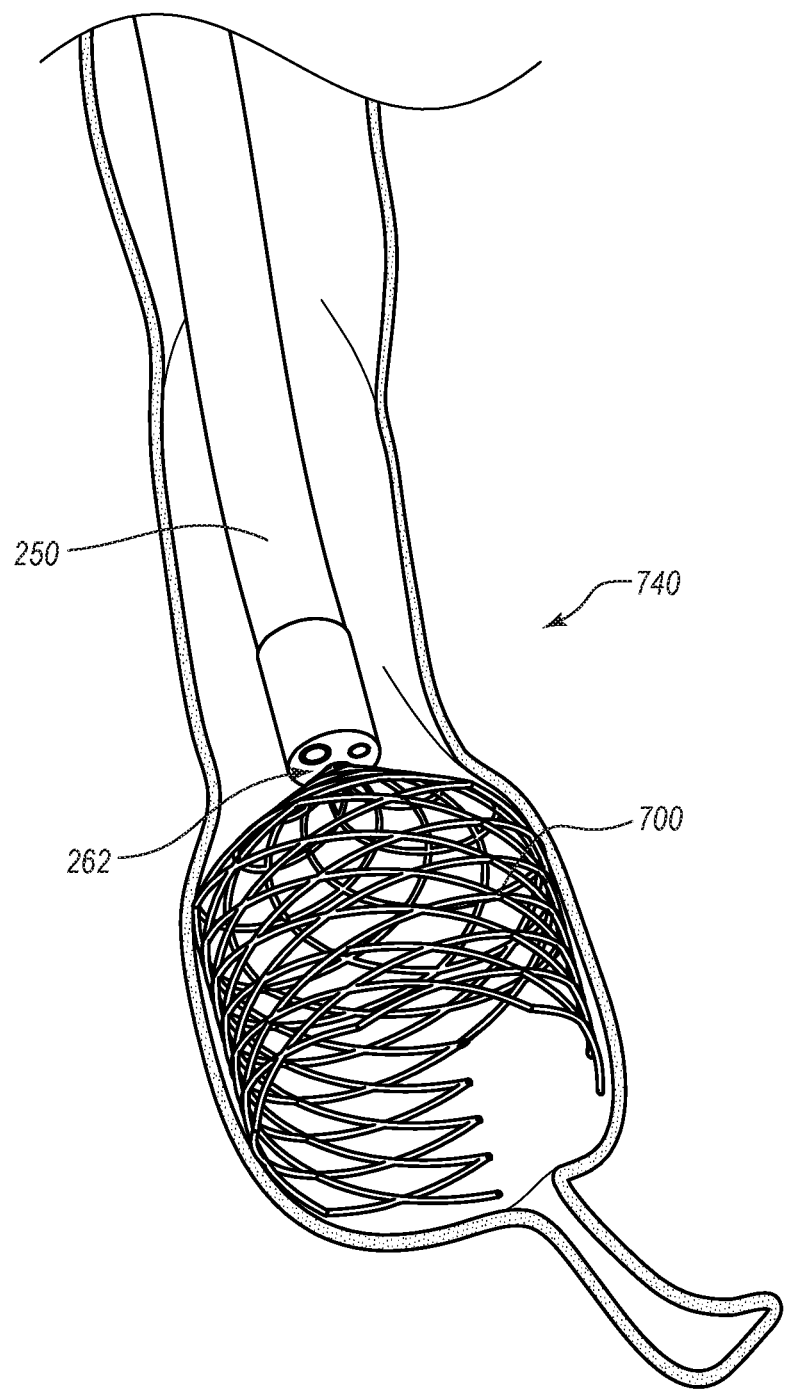
FIG. 7A is a cross-sectional view of a portion of the colon of a patient during another illustrative method in which a stent, shown in perspective, is being delivered to the cecum of the patient directly from an instrument channel of an endoscope, also shown in perspective.
Figure 7B:
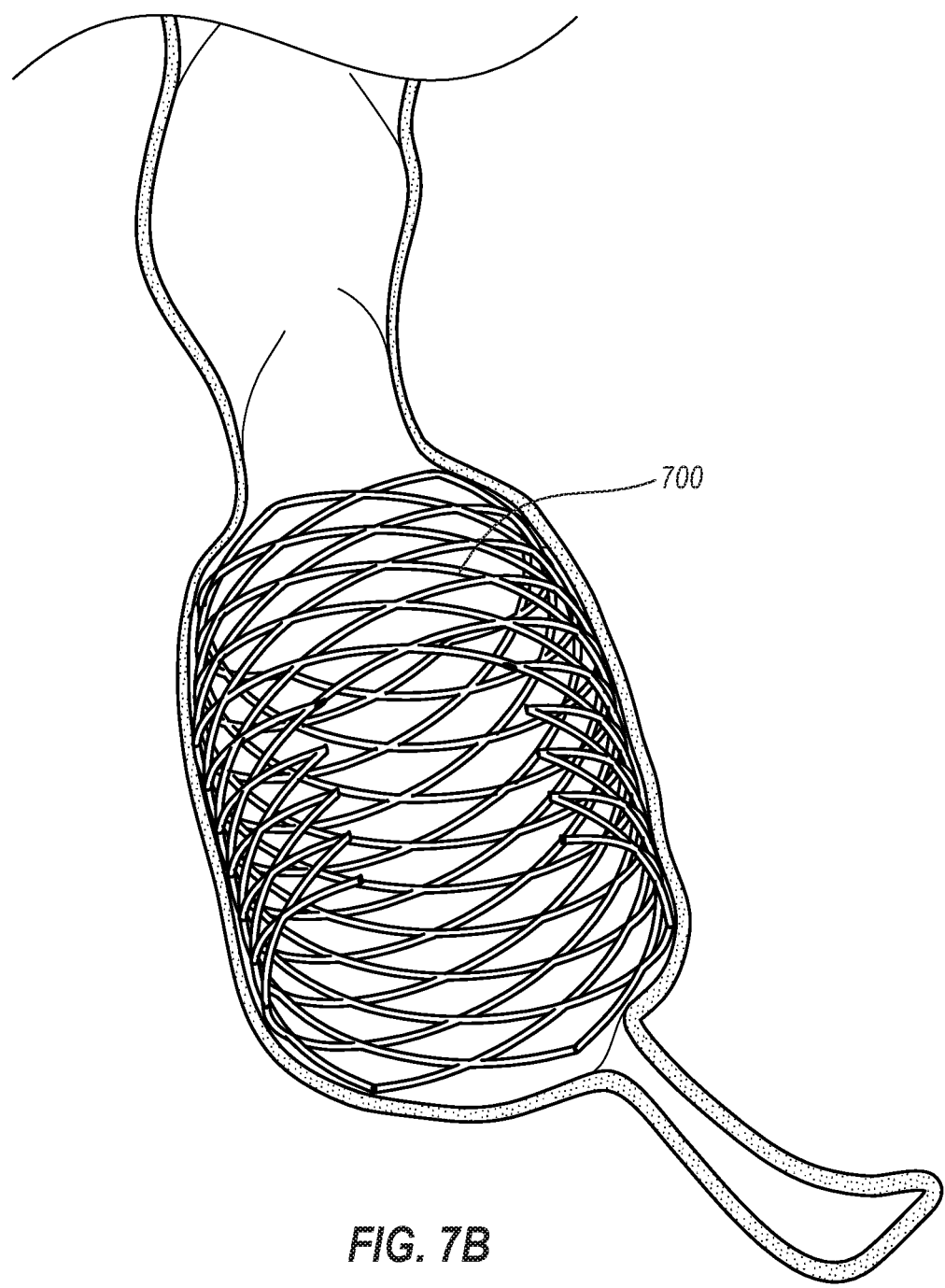
FIG. 7B depicts another stage of the method in which the stent has been deployed and the endoscope has been removed from the patient.

FIGS. 7A and 7B depict stages of an illustrative method for using a system 740 to introduce a medical device or stent 700 into the patient 205. The system 740 can include the endoscope 250, the stent 700, and a deployment mechanism (not shown) for advancing the stent 700 from the channel 262 of the endoscope 250. The method can be substantially the same as that discussed above with respect to FIGS. 5A-5E. However, rather than inserting a balloon catheter through the instrument channel 262 of the endoscope 250 to deploy the stent, in the instant method, the stent 700 is self-expanding and may itself be advanced through instrument channel 262 and can be deployed directly from the instrument channel 262. For example, in some embodiments, the stent 700 may be positioned at the tip of the endoscope 250 prior to insertion of the endoscope 250 into the patient 205. Once the tip of the endoscope 250 is in the desired position, the stent 700 can be pushed out of the channel 262 in any suitable manner (e.g., may be pushed by a wire or other suitable deployment mechanism) and can expand automatically once no longer restrained within the channel 262. In other or further instances, a restriction sleeve may be removed from the stent 700 prior to or during deployment. In still other or further instances, the stent 700 may be pushed through a larger portion of the channel 262 (e.g., an entirety thereof) after the tip of the endoscope has been positioned as desired.

Figure 8A:
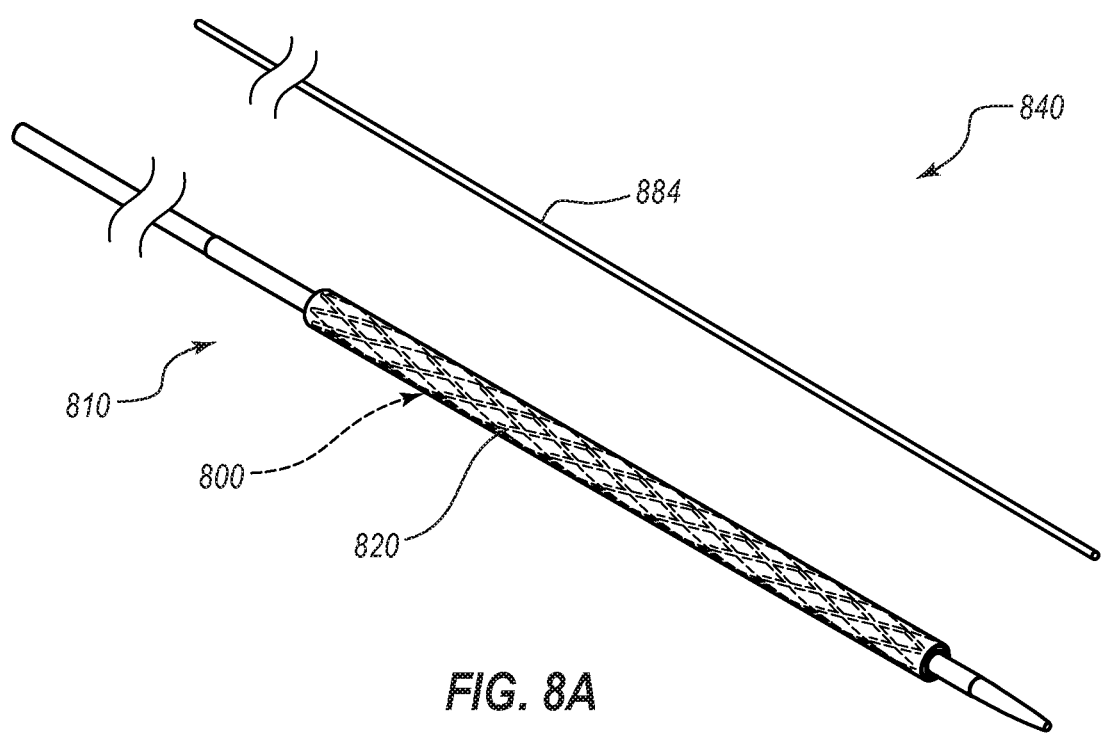
FIG. 8A is a perspective view of another embodiment of a system that can be used to implant an embodiment of an expandable medical device within the bowel of a patient.
Figure 8B:
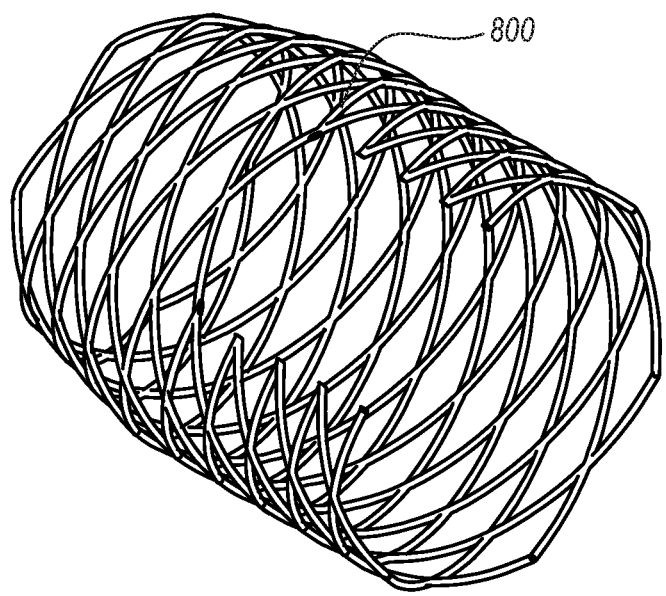
FIG. 8B is a perspective view of the expandable medical device in a deployed or expanded state.

FIGS. 8A and 8B depict an illustrative system 840 for implanting an embodiment of a self-expanding stent 800. The system 840 includes a catheter 810 to which a stent 800 is coupled. Unlike the catheter 510, in which the stent is positioned over an expandable balloon, the stent 800 is instead resiliently biased outward so as to naturally assume an expanded position upon removal of a retention sleeve 820 that is positioned about the stent 800. The method for introducing the stent 800 into the bowel 200 of the patient 205 can be substantially the same as that discussed above with respect to FIGS. 5A-5E. However, rather than passing the catheter through the instrument channel of the endoscope, the catheter 810 is advanced along the guidewire 884. For example, in some methods, the guidewire 884 may be advanced through the bowel of the patient 205 to a desired position in the bowel (e.g., via fluoroscopic or other imaging assistance). Once in place, the guidewire 884 may be positioned within an internal or external lumen defined by the catheter 810, and the lumen may be advanced over the guidewire 884 until the catheter is in the desired position. The restrictive sleeve 820 may then be removed, such as by retraction of a wire attached thereto, and the self-expanding stent 800 can naturally expand outwardly into contact with the bowel to distend the bowel, as it assumes the deployed or expanded configuration depicted in FIG. 8B.

In the present example, the stent 800 can be placed without using an endoscope. In other instances, the guidewire 884 may be positioned in the patient in the manner just discussed, and then an endoscope can be advanced over the guidewire into position. For example, the guidewire may pass through the instrument channel of the endoscope. The guidewire may then be removed, and the catheter 800 may then be advanced through the instrument channel of the endoscope. Any other suitable techniques for positioning the stent in the patient are also contemplated.

Figure 9:
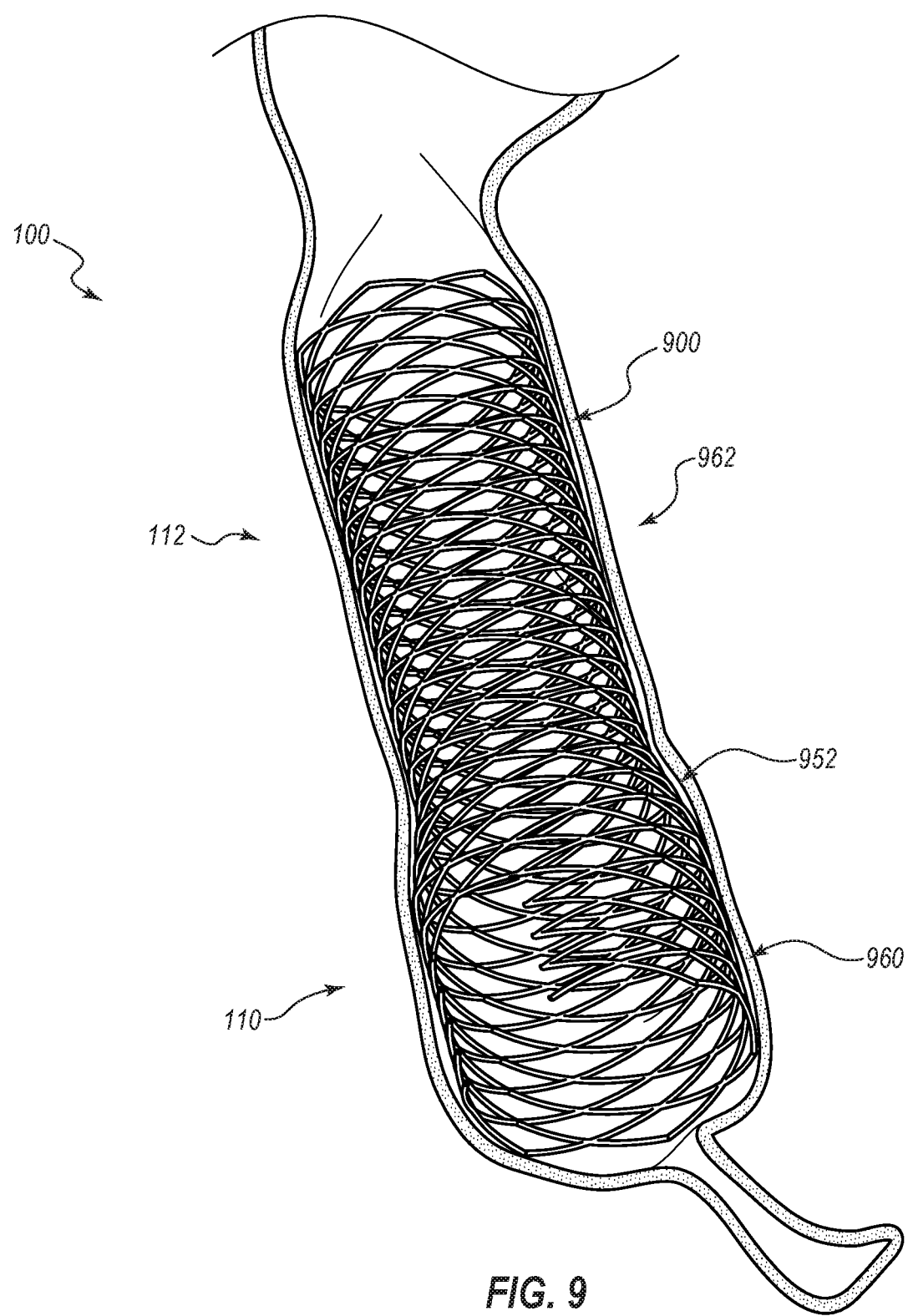
FIG. 9 is a cross-sectional view of a portion of the colon of a patient in which another embodiment of a stent, shown in perspective, has been delivered.

FIG. 9 depicts another embodiment of a stent 900 implanted in the colon 100 of the patient 205. Specifically, a bulbous portion at a proximal end of the stent 900 is positioned in the cecum 110, and an elongated distal extension 962 of the stent 900 extends into the proximal portion of the ascending colon 112. In the illustrated embodiment, a proximal portion of the stent 900 is substantially identical to the stent 500. The primary difference between the two stents is the distally directed extension 962, which resides within the ascending colon 112. The stent 900 includes a taper 952 that can prevent migration in manners previously discussed. The stent 900 can be less prone to rotation about non-longitudinal axis than the stent 500. The stent 900 can be configured to distend one region of the bowel (e.g., either the cecum 110 or the ascending colon 112) proportionally more than another portion. For example, in some embodiments, the distal extension 962 of stent 500 primarily serves as anchoring leg for the stent 500, and may provide the ascending colon 112 with little or no distention, whereas the proximal end of the stent 900 may significantly distend the cecum 110 to trigger an intestinal-gastric brake. In other embodiments, both ends of the stent 900 can distend the respective regions of the bowel 200, and may each contribute to the intestinal-gastric brake. In some embodiments, one end of the stent 900 expands the bowel by a percentage that is greater than a percentage by which the other end expands the bowel, or in other embodiments, both ends can yield similar distention percentages.

Figure 10A:
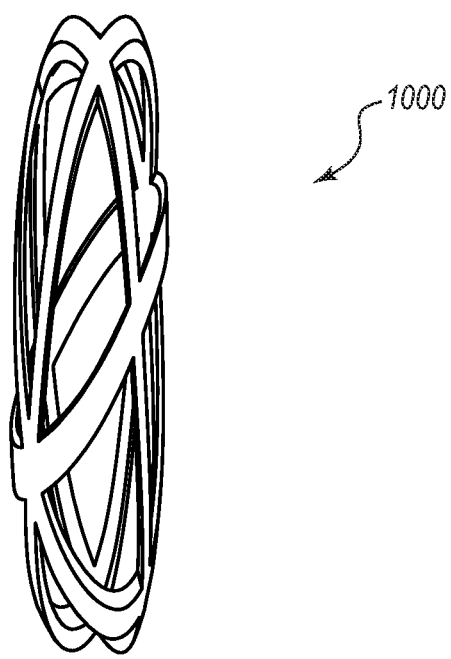
FIG. 10A is a perspective view of another embodiment of a medical device for the treatment of obesity, wherein the medical device is depicted in a contracted or undeployed state.
Figure 10B:
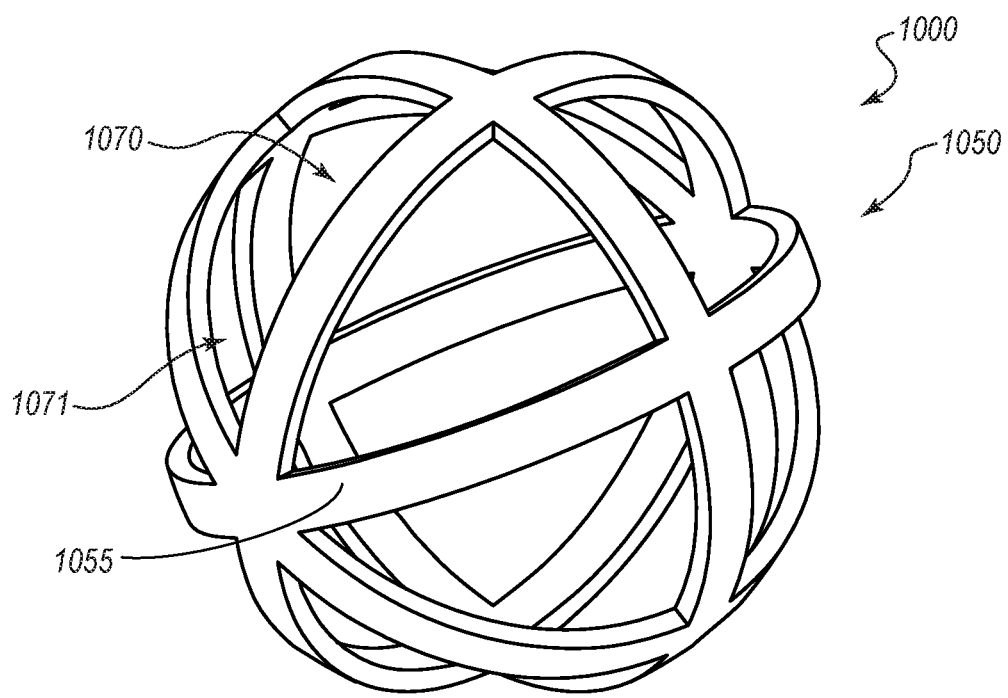
FIG. 10B is another perspective view of the medical device that depicts the device in an expanded or deployed state.

FIGS. 10A and 10B depict another embodiment of a medical device 1000, which may also be referred to herein as a stent ball or as a cage. The device 1000 is depicted in an undeployed, constricted, or unexpanded state in FIG. 10A, and is depicted in a deployed configuration in FIG. 10B. In some embodiments, the device 1000 can be expanded and can distend a portion of the bowel 200, such as the cecum 110, in manners similar to the stents previously discussed. For example, in some embodiments, the device 1000 may be deployed directly from an endoscope lumen or from a catheter lumen. The device 1000 may be formed of any suitable material, whether self-expanding or expandable with, e.g., balloon assistance. For example, in various embodiments, self-expanding versions may comprise Nitinol or other shape-memory material to expand from the generally tubular constricted configuration to the generally spherical expanded configuration once within the bowel.

The device 1000 can include a body 1050, which may be defined by a series of interconnected struts 1055, which have a substantially rectangular cross-sectional profile. The struts 1055 can define a plurality of openings 1071 of a passageway 1071 thorough the device 1000. The illustrated embodiment includes 12 total wedge-shaped openings 1071. The openings 1071 and passageway 1071 are relatively large, and thus are capable of permitting a large flow rate of material to pass through when the device 1000 is implanted.

Figure 11:
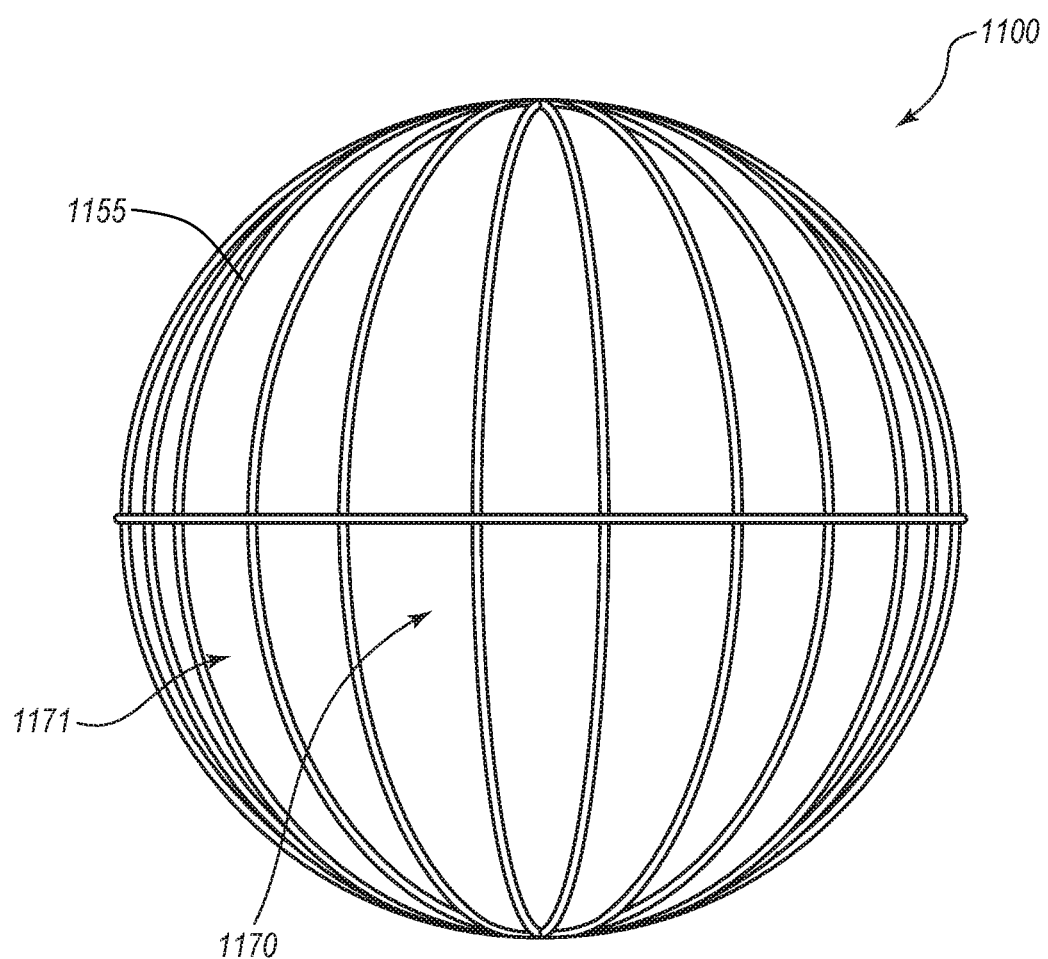
FIG. 11 is a perspective view of another embodiment of a medical device for the treatment of obesity.

FIG. 11 depicts another embodiment of a device 1100, which can resemble the device 1000 in many respects, and can be a mechanical self-expandable or otherwise expandable cage. The device 1100 may include a plurality of interconnected struts 1155 that may be formed and connected in any suitable manner. In the illustrated embodiment, the struts 1155 are formed as wires or rods with substantially circular cross-sectional profiles.

The struts 1155 define a plurality of openings 1171 of a passageway 1070. The illustrated embodiment includes 44 total wedge-shaped openings 1071. Other numbers and configurations of the openings 1071 are contemplated. The openings 1171 and passageway 1171 are relatively large, and thus are capable of permitting a large flow rate of material to pass through when the device 1100 is implanted.

As with other devices disclosed herein, in some embodiments, the device 1100 can be made of material that is biodegradable or bioresorbable over time, and thus may eventually naturally pass from the patient 205. In other or further instances, the device 1100 may be retrievable from its implantation site. For example, the device 1100 may be readily collapsible via mechanical manipulation.

Figure 12:
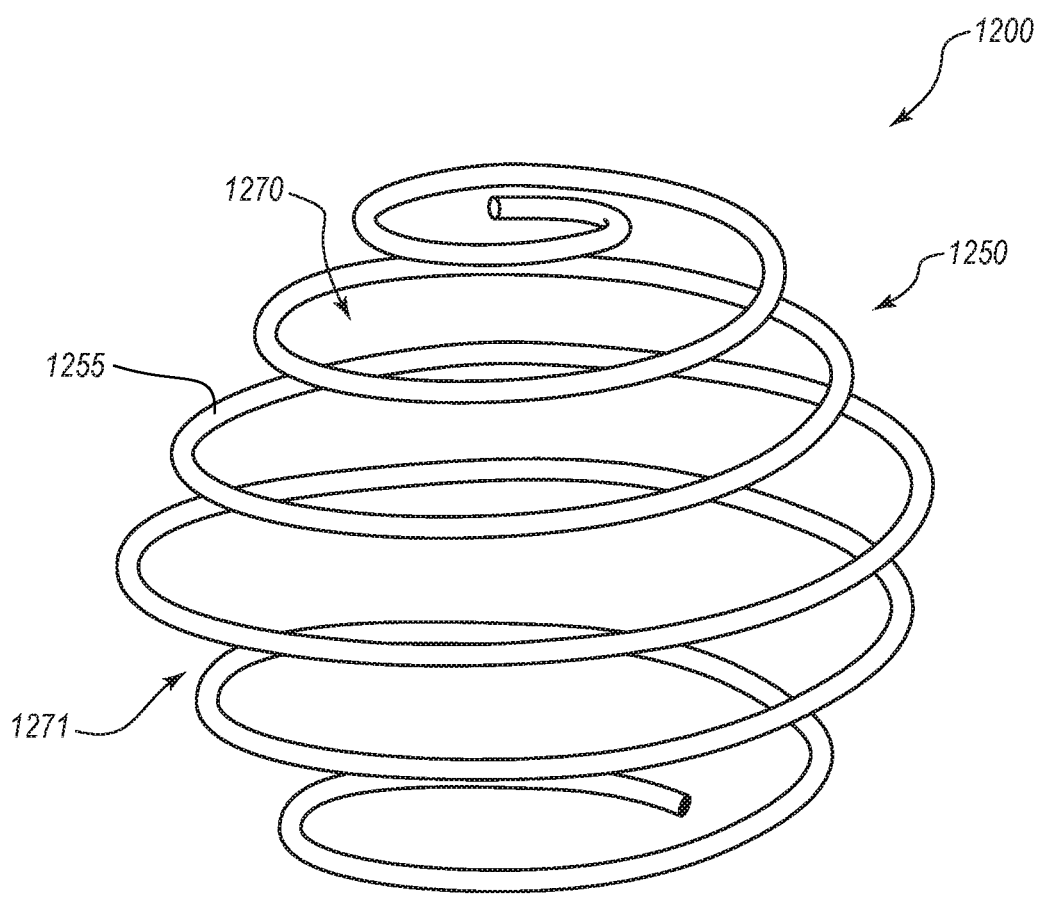
FIG. 12 is a perspective view of another embodiment of a medical device for the treatment of obesity.

FIG. 12 depicts another embodiment of a medical device 1200 that likewise resembles a cage. The device 1200 includes a frame or body 1250 that is formed from a single rod or wire 1255. The wire 1255 is wound or spiraled in a somewhat spherical shape, or may be termed as a spiral ball. The wire 1255 defines an extended opening 1271 of a passageway 1270 that passes through the ball. In particular, the opening 1270 is likewise spiral shaped.

As with other embodiments described herein, the device 1200 can comprise any suitable material, and may be self-expandable or may expand with assistance (e.g., via any suitable mechanical manipulation, such as balloon expansion). Illustrative examples include metals and/or plastics or any suitable variety, nanomaterials, etc. In some embodiments, the device 1200 comprises any suitable shape-memory material (e.g., Nitinol).

In some embodiments, the device 1200 may be introduced through the lumen of a catheter or endoscope. For example, in some instances, the device 1200 may be in a straightened configuration (e.g., have a substantially linear form) when in an undeployed or unexpanded configuration, and can be advanced through the lumen of the catheter or endoscope in this orientation. Once having exited the lumen into the desired position within the bowel, the device 1200 may naturally (e.g., if formed of a shape-memory material) transition (e.g., return) to the space-filling, volume-defining, expanded ball shape depicted in FIG. 12 and distend the bowel.

In other embodiments, the device 1200 may be formed of a material that is configured to expand due to absorption of material (e.g., water) within the bowel. For example, in some embodiments, the device comprises a superabsorbent polymer. The polymer can function the same as or similar to expandable water toys, also known as grow-in-water toys. For example, the device may be sponge-like when in an undeployed state. The device 1200 could be inserted into the bowel in a "dry" (or low moisture content) condition, and then can expand when exposed to water or colonic effluent once introduced into the bowel. In some embodiments, the device 1200 can expand sufficiently to distend a portion of the bowel.

In other or further embodiments, a variety of coatings and/or compositions may be applied to the frame of the device 1200. As with other devices, the materials can elute beneficial substances, such as appetite suppressants. For example, in some embodiments, the device 1200 is coated with a polyethylene glycol resin that contains, e.g., a complex carbohydrate or other nutrient source for the patient 205 directly, or contains, e.g., cellulose or some other material that provides nutrients for bacteria that reside in the bowel. Bacteria could eat and derive nutrients from the material over time, and may be sufficient to independently achieve or to assist in achieving satiety for the patient. Items like cellulose may be advantageous, as they need not be preserved (e.g., refrigerated) prior to implantation. In some embodiments, the material that may be eluted can comprise nutrients for the patient 205, such as, for example, any suitable complex carbohydrate, simple carbohydrate, fat, or protein. In other or further embodiments, the material that may be eluted can comprise nutrients for bacteria, either including or in exclusively, some materials that are non-nutritive for the patient, such as, for example, cellulose or *psyllium*.

In some embodiments, a pouch or other container is positioned at interior of the device 1200. For example, the pouch may comprise a millipore netting or the like that is positioned within the frame or body 1250. The pouch can include nutrients that leach out or are otherwise consumed over time. Nutrients or other materials can be consumed over time and assist in satiating the patient. In other or further embodiments, the body 1250 is independently formed of a separate bioresorbable material that degrades over time and, eventually, spontaneously passes out through the bowel and out of the patient 205.

FIGS. 13A-13G depict additional embodiments of devices 1300, 1301, 1302, 1303, 1304, 1305, 1306 that can be implanted in the patient 205 to trigger an intestinal-gastric brake, such as by transitioning from an undeployed or unexpanded state to an expanded state in which the device distends a portion of the wall of the bowel. The devices 1300-1306 may also be referred to as cages, shells, balls, or balloons.

Each device 1300, 1301, 1302, 1303, 1304, 1305, 1306 can include a body 1350 that defines a plurality of openings 1371 that are in fluid communication with a cavity of the body 1350. The cavity is a passageway 1370 through which material can pass. The size, shape, number, pattern (or lack thereof), and/or orientation of the openings 1371 can be varied, depending on, for example, performance preferences. The devices 1300, 1301, 1302, 1303, 1304, 1305, 1306 are illustrative a wide variety of possible options for different sizes, shapes, numbers, patterns, and/or orientations of the openings. The openings 1370 can be any shape or size. The openings 1371 and the passageway 1370 of each device can permit passage of material through the body 1350.

In some embodiments, the body 1350 is a hollow shell of material. The shell may be relatively thin. In some embodiments, the material of which the body 1350 is formed is resiliently flexible or elastomeric. For example, in some embodiments, the body 1350 can be compressed or otherwise compacted to a smaller profile to transition the device to the undeployed state. Upon placement in the bowel, the body 1350 can be released from the compressed state and can naturally transition to the deployed or expanded configuration.

The body 1350 can define a variety of different shapes or configurations. In FIGS. 13A-13E, the bodies 1350 each define a substantially spherical outer surface that is perforated by the various openings 1371. In FIGS. 13F and 13G, the bodies 1350 are more oblong. In some instances, the oblong shapes may more readily conform the pouch-like configuration of the cecum and/or may be less susceptible to rotation (e.g., rotation about axes other than a longitudinal axis of the body) when retained in the bowel in a free-floating arrangement.

The set of openings 1371 and the passageways 1370 with which they communicate can be sufficiently large to permit material that would naturally pass through the portion of the bowel in the absence of the body 1350 to pass through the body 1350 substantially unimpeded. In some embodiments, the body 1350 is multi-chambered, and thus may define multiple passageways. All such passageways may desirably provide sufficient flow capacity to permit material that would naturally pass through the portion of the bowel in the absence of the body 1750 to pass through the body 1750 substantially unimpeded.

In various embodiments, the body 1750 is configured to obstruct no greater than 5, 10, 15, or 20 percent of material from passing through the portion of the bowel within which the body 1750 is positioned. In various embodiments, the body 1750 is configured to reduce a flow capacity through a lumen defined by the portion of the bowel by no greater than 10, 20, 30, 40, or 50 percent.

Figure 13A:
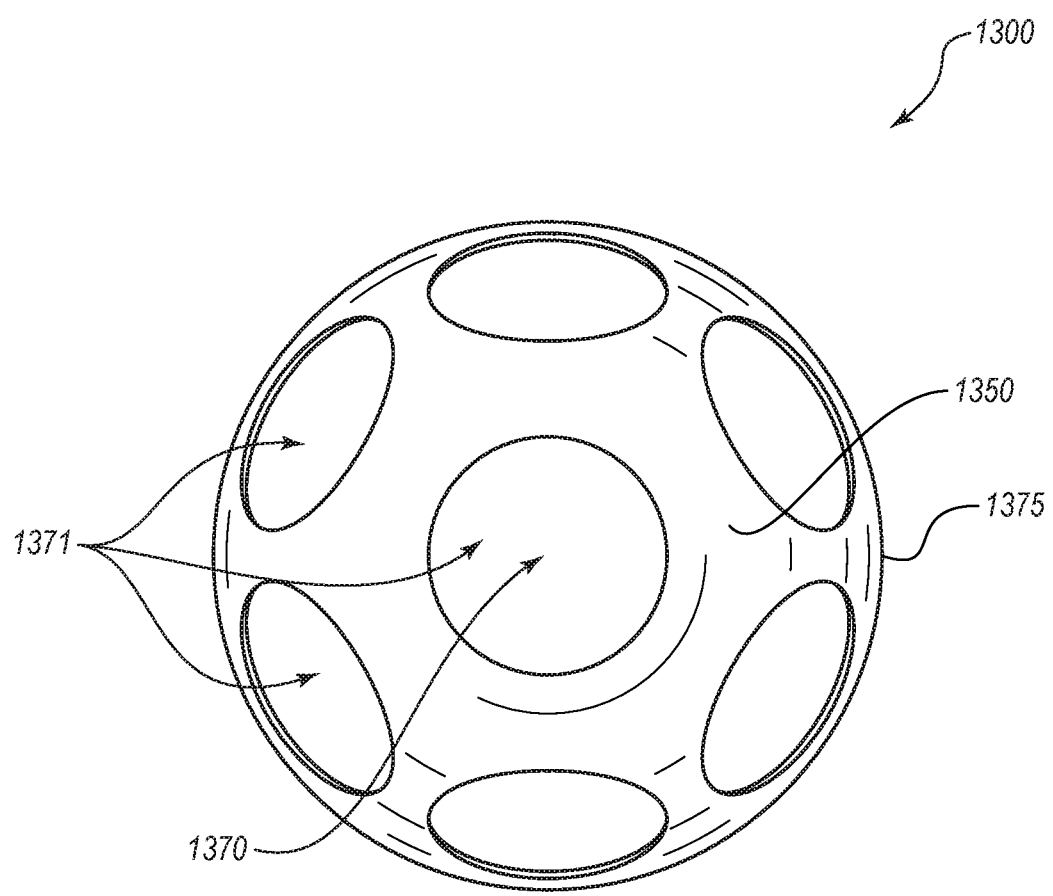
FIGS. 13A-13G are perspective view of additional embodiments of medical devices for the treatment of obesity.
Figure 13B:
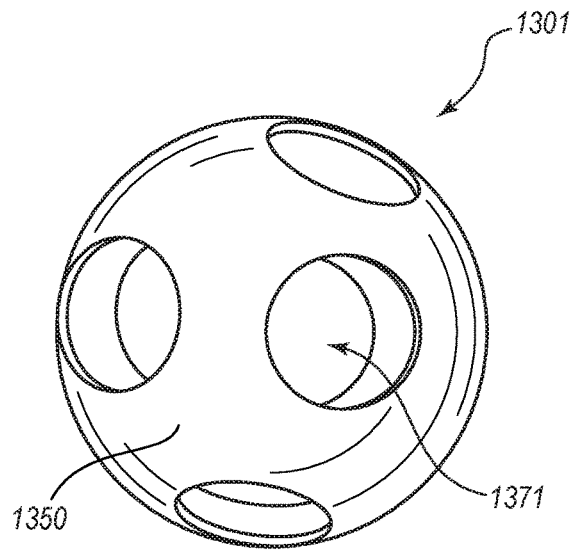
Figure 13C:
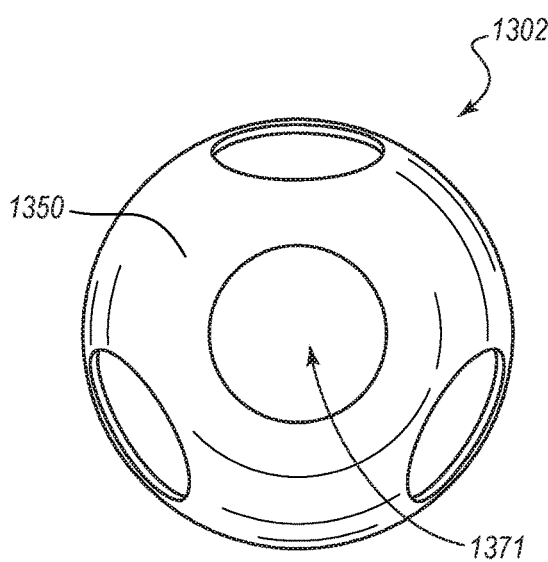
Figure 13D:
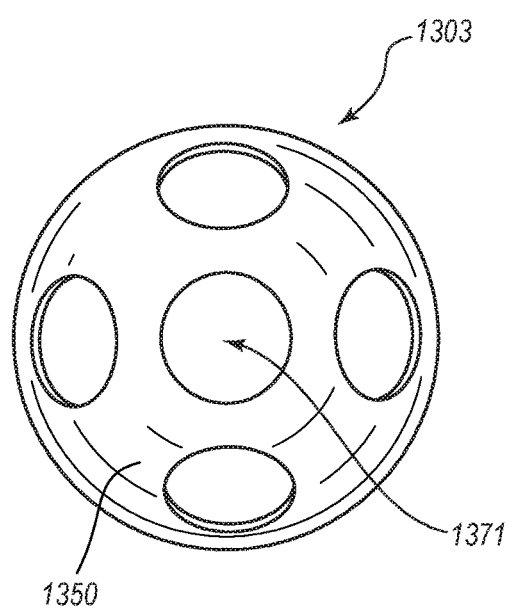
Figure 13E:
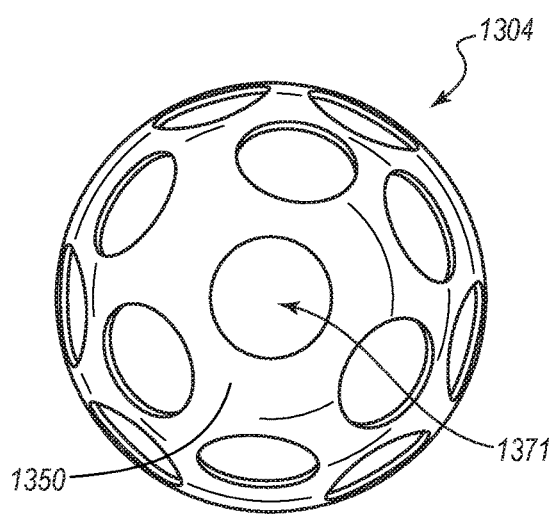
Figure 13F:
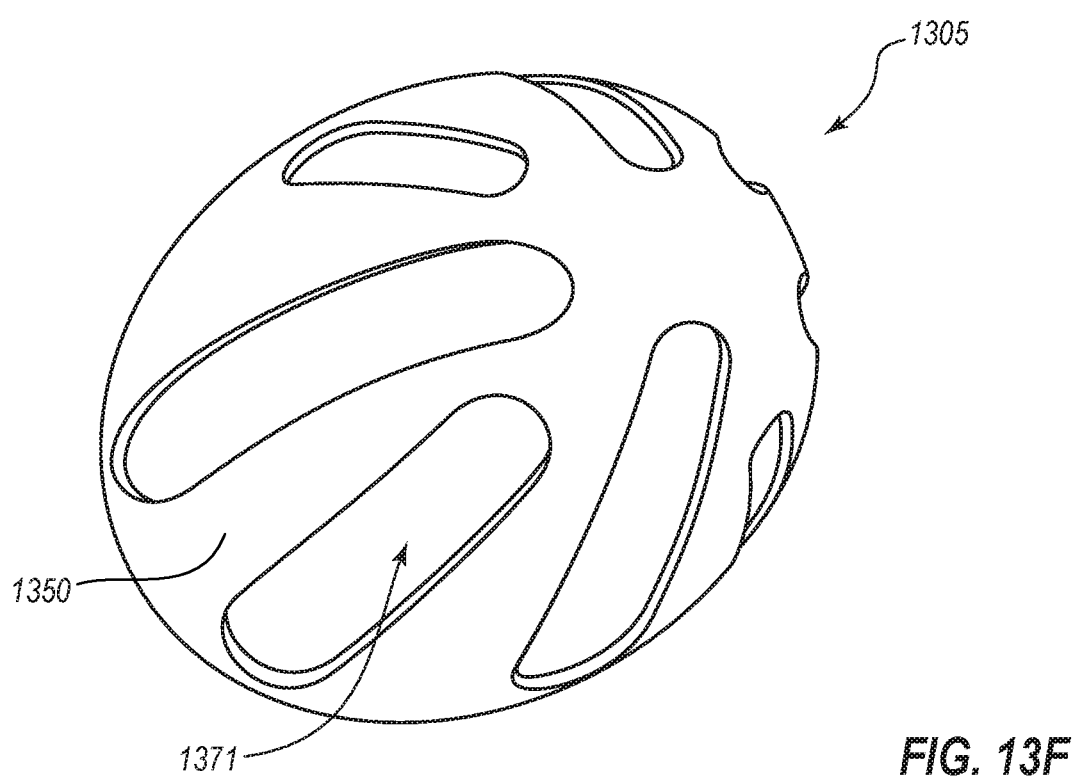
Figure 13G:
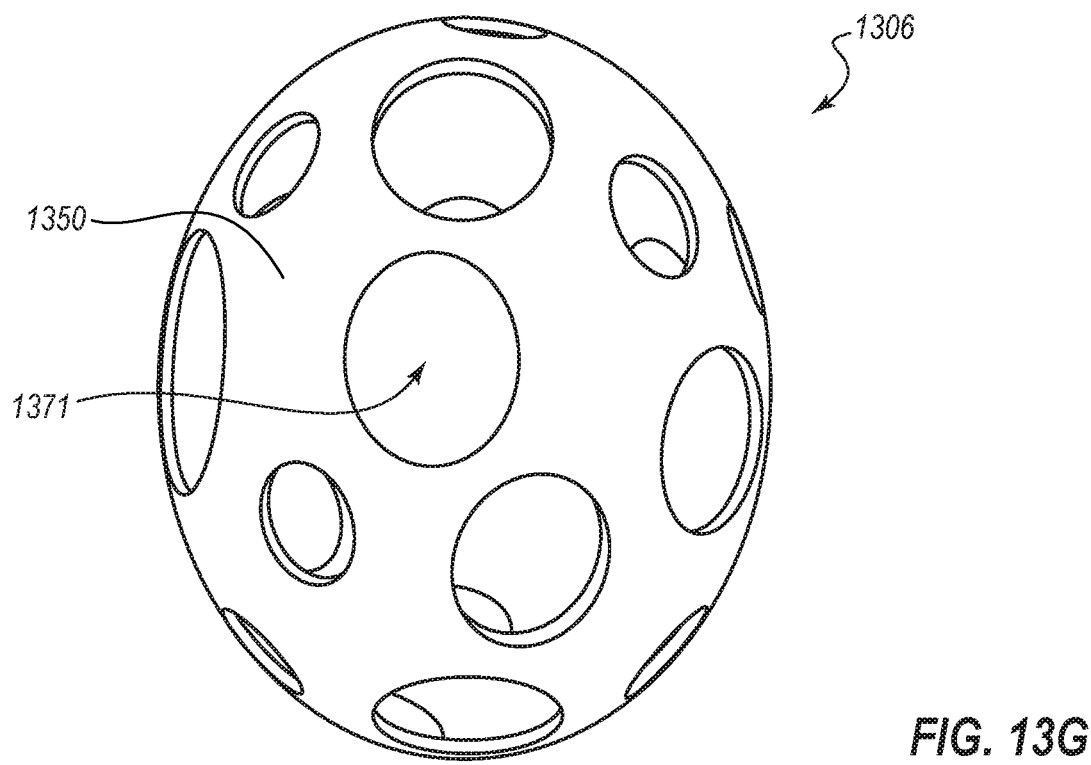

With reference to FIG. 13A, the body 1750 can define an outermost perimeter 1375. In some instances, the outermost perimeter 1375 contacts the bowel as the body 1750 distends the bowel. For example, in some instances, the perimeter 1375 of the body 1750 may be fully in contact with an inner surface of the bowel. Stated otherwise, the body 1750 may contact the bowel about the full perimeter 1375 (or periphery), and a full perimeter of an inner surface of the bowel may contact the perimeter 1375. For example, the device 1300 could be positioned within a lumen of the bowel such that a longitudinal axis of the lumen is substantially aligned with an axis that passes directly through the center of the device 1300 and is perpendicular to the plane of the page of FIG. 13A. In further instances, such as when the device 1300 is in full contact with the bowel and/or distends the portion of the bowel with which it is in contact, the bowel wall can be in contact with the full perimeter 1375. In certain of such instances, it may be said that the body 1370 define a longitudinal axis (e.g., longitudinal relative to its position in the lumen) that is substantially aligned with a direction of material flow through the passageway 1370.

In some embodiments, the perimeter 1375 of the body 1350 defines a maximum cross-sectional area along a plane that is transverse to the longitudinal axis of the body 1350. For example, in the illustrated embodiment, this plane is the plane of the page. It may also be said that the passageway 1370 defines a minimum cross-sectional area along a different plane transverse to the longitudinal axis. As an example, the passageway 1350 has a minimum area at the opening 1371, which is on a plane that is parallel to the plane of the page. In various embodiments, the minimum cross-sectional area defined by the passageway 1370 (e.g., the area of the opening 1371) is smaller than the maximum cross-sectional area defined by the body by no greater than 10, 20, 30, 40, 50, 60, 70, 80, or 90 percent. With respect to the stents depicted in the drawings, the lumen size can be substantially the same as the lumen size of the bowel. With respect to the device 1300 of FIG. 13A, however, the minimum size of the passageway 1370 is substantially smaller than the size of the perimeter 1375. In certain embodiments (e.g., a cylindrical tubular stent), the planes of maximum perimeter and minimum passageway size may be coplanar.

In some embodiments, a summation of the areas defined by the entrance openings 1371 of the passageways is smaller than the maximum cross-sectional area defined by the body 1350, along a plane transverse to the longitudinal axis (e.g., a transverse plane through the bowel lumen when the device is implanted therein) by no greater than 10, 20, 30, 40, or 50 percent. This ratio of areas can be a good indication of the amount of flow reduction that may be caused by the presence of the device 1300, in some instances.

Figure 14A:
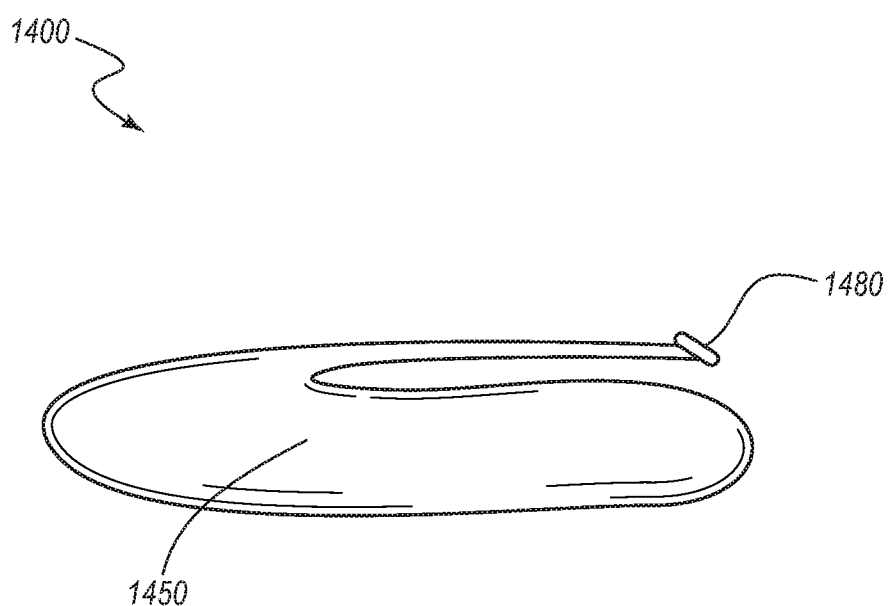
FIG. 14A is a perspective view of another embodiment of a medical device for the treatment of obesity, wherein the medical device is depicted in a contracted or undeployed state.
Figure 14B:
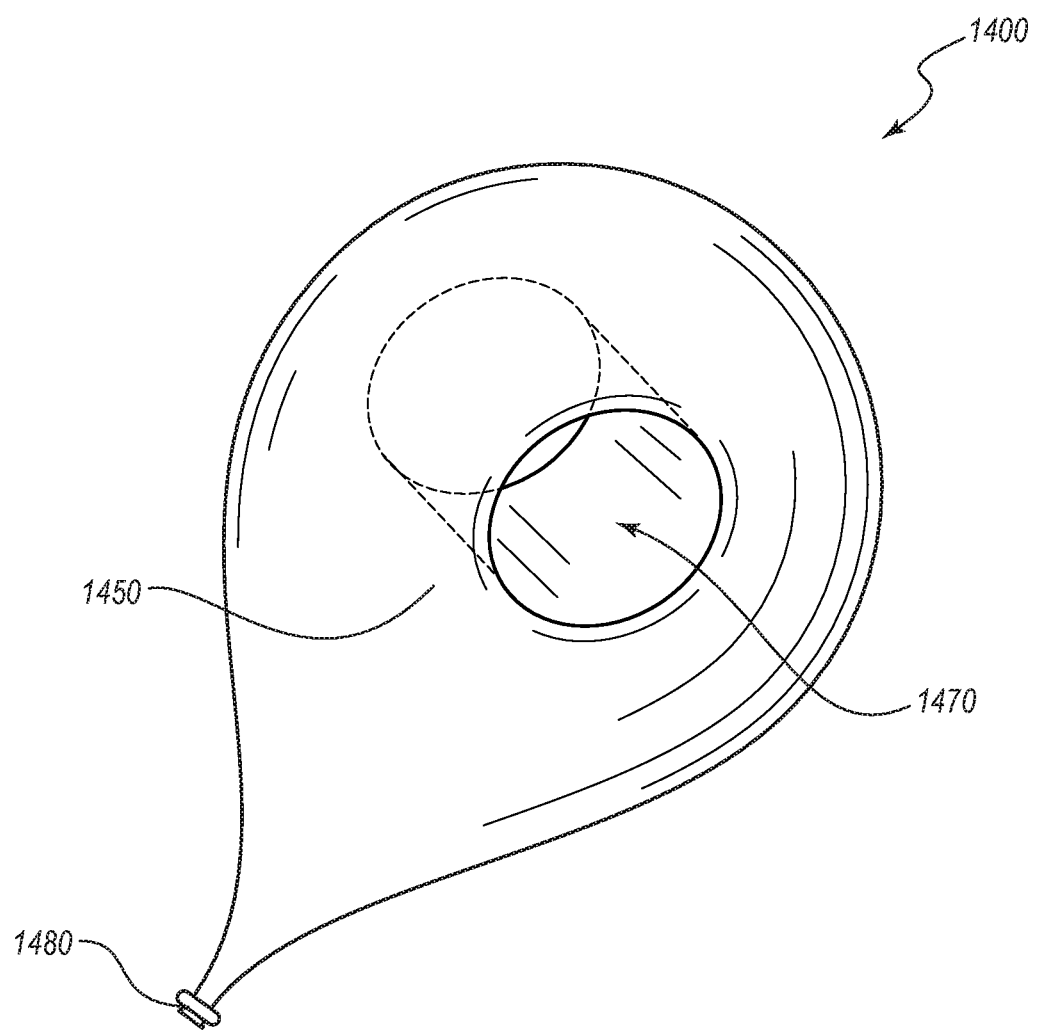
FIG. 14B is another perspective view of the medical device that depicts the device in an expanded or deployed state.

FIGS. 14A and 14B depict another embodiment of a medical device 1400 or structure that is formed as a balloon with an integrated channel. The device 1400 can be inflated at the desired location and/or inflated and delivered thereto.

The device 1400 includes a body 1450 that defines a channel 1470 when in the expanded state. The structure can be self-sealing, such as via any suitable closure 1480, such as a one-way valve. For example, in some embodiments, the closure 1480 includes a one-way valve through which fluid is introduced into the body 1450, and then subsequently maintained in the balloon. In various embodiments, the body 1450 can be advanced into the bowel in a deflated or partially deflated state. The body 1450 may, for example, be delivered to a desired site over a guidewire, over or through an endoscope, or in any other suitable manner. The structure can be applied in a specific segment of the bowel and take 3-dimensional shape when inflated in order to distend the lumen.

In various embodiments the body 1450 is formed of latex, nonlatex, rubber, derivatives of rubber, any rubber-like material or elastomeric material, or any other suitable material. The body 1450 can be expanded with one or more fluids (e.g., air or saline). Once inflated, the body 1450 may be either free floating in the lumen of the bowel or attached or otherwise secured to the wall of the bowel. For example, in some instances, the body 1450 may be attached to the wall by sutures or an adhesive. In other or further embodiments, the body 1450 may be tensioned in place by achieving a suitable pressure of the inflation fluid. The balloon can be expanded to a variety of sizes or shapes, causing a variety of distention amounts of the bowel.

In some embodiments, at least a portion of the balloon body 1450 comprises a material that is degradable over time (e.g., any suitable bioresorbable material). Degradation can yield leaks in the walls, leading to loss of fluid and size reduction. In other or further embodiments, at least a portion of the closure 1480 comprises a degradable material, which can yield a leak by which the device 1400 is deflated and may eventually spontaneously pass from the patient.

In some embodiments, in order to prevent bowel obstruction from the balloon, the balloon includes the channel 1470. It may be desirable to orient the balloon such that the channel 1470 is substantially aligned with a longitudinal axis of the bowel lumen. The bowel lumen thus can be simultaneously expanded by the balloon, yet the balloon passageway or channel 1470 can allow air, liquid, semiliquid, semi-solid or solid stool to pass therethrough.

Figure 15:
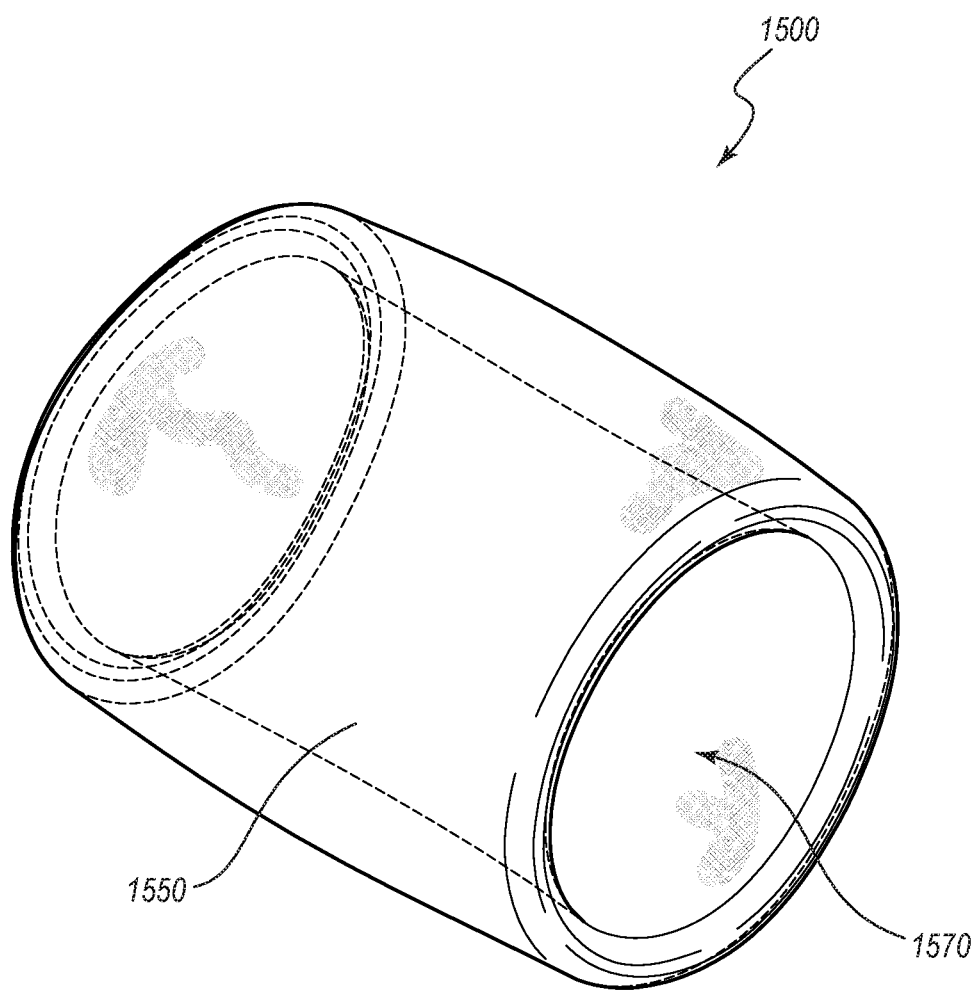
FIG. 15 is a perspective view of another embodiment of a medical device for the treatment of obesity, wherein the medical device is depicted in an expanded or deployed state.

FIG. 15 depicts another embodiment of a device 1500 that can include an inflatable balloon body 1550, which may also include a self-sealing closure (such as the valve 1480 previously described). The body 1550 defines a large central passageway 1570.

The shape of the body 1550 may assist in ensuring that passageway 1570 remains aligned with the lumen of the bowel. For example, the illustrated embodiment may fit well in the pouch-like cecum, and a length of the body 1550 is such that rotation of the device relative to the bowel in a manner that could close the passageway 1570 would be inhibited.

Figure 16:
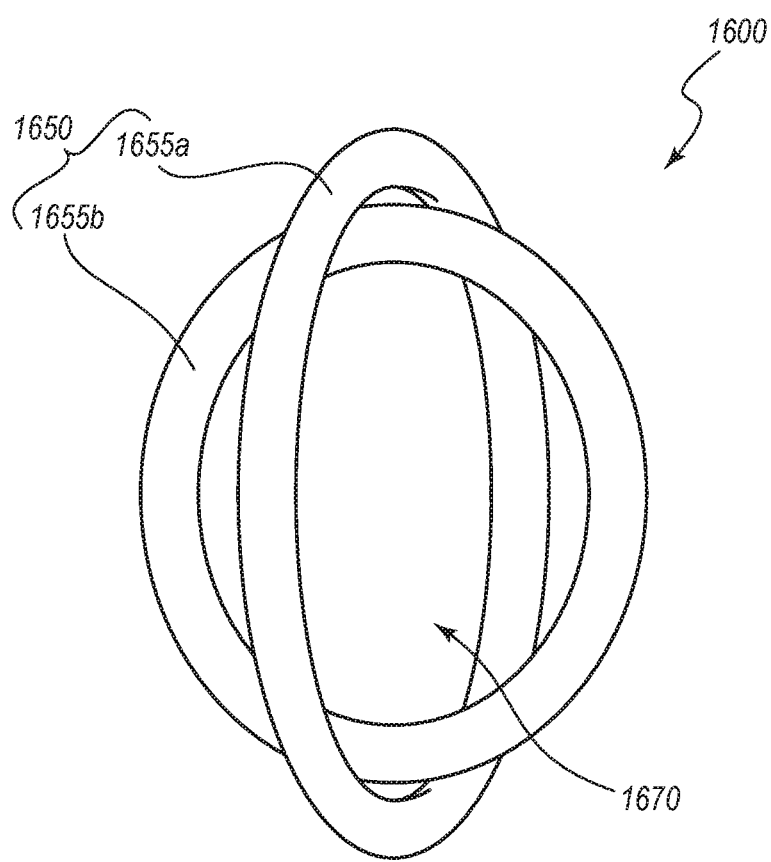
FIG. 16 is a perspective view of another embodiment of a medical device for the treatment of obesity.

As shown in FIG. 16, another example structure or medical device 1600 can include a plurality of inflatable structures 1655a, 1655b that define a body 1650 of the device. The body 1650 defines a passageway 1670 through which material can pass when the device 1600 is implanted. The structures 1655a, 1655b are each substantially tubular rings that are oriented perpendicularly to each other, such as to form an atom shape. In various embodiments, the device 1600 can include two attached or interlocking circular or hemi-circular balloons. Other arrangements are possible, such as discussed further below. The structures 1655a, 1655b can be oriented relative to each other in a manner to allow wide openings between the individual balloons.

In the illustrated embodiment, each structure 1655a, 1655b is self-contained. Or stated otherwise, each structure 1655a, 1655b defines a separate chamber. Thus, the body 1650 is a two-chamber system, with each chamber being separate from the other. In some embodiments, each structure 1655a, 1655b contains a self-sealing or auto-closing closure, and each structure 1655a, 1655b may be inflated separately. The structures 1655a, 1655b may be attached to each other in any suitable manner. In some embodiments, the structures 1655a, 1655b are secured to each other via a bioresorbable material, such as a bioresorbable adhesive.

Embodiments can thus include multiple circular or hemi-circular interlocking balloons in any manner or shape that would allow expansion of the balloons but also allow for spaces or openings between the balloons, such as the example structures shown in FIGS. 17-20.

In other embodiments, configurations other than circular or hemi-circular are used. Any suitable geometric shape in combination with any other shapes are contemplated. Thus, the balloon could be partially circular or circular or hemi-circular in combination with any other shape or shapes, so long as there are spaces or perforations between or in the balloon or balloons to allow air or fluid or liquid or semi-liquid or semi-solid stool to pass. The balloons or portions of the balloons could be as thin as ribbons or tubular or any thickness or size. Thus, the combination of balloons is essentially limitless as long as there are spaces incorporated within the design to allow passage of air, solid, or liquid.

In other embodiments, the structures 1655a, 1655b are connected so as to define a single chamber. Accordingly, the body 1650 can be inflated via a single port.

In certain embodiments, the material of which the body 1650 is formed can degrade which can lead fluid to escape and the body to deflate. In other or further embodiments, the structures 1655a, 1655b are held together by material that degrades or deflates. For example, a bioresorbable material can hold together the separate structures 1655a, 1655b prior to degradation, and degradation of the bioresorbable material releases the separate pieces from each other. One or more of the deflated and/or degraded structures 1655a, 1655b, or individual pieces thereof, can pass through the bowel and be eliminated spontaneously. In other or further embodiments, the body 1650 can be removed endoscopically.

More generally, with respect to various embodiments disclosed herein, connections between various facets of the structure, such as connections holding two or more balloons together, or two or more mechanical features together (such as certain of the struts 555 [see FIG. 5E], 1055 [see FIG. 10B], 1155 [see FIG. 11]), could degrade or deflate over time, allowing for separation of the structure and partial or complete elimination of the structure in stool over time.

Figure 17:
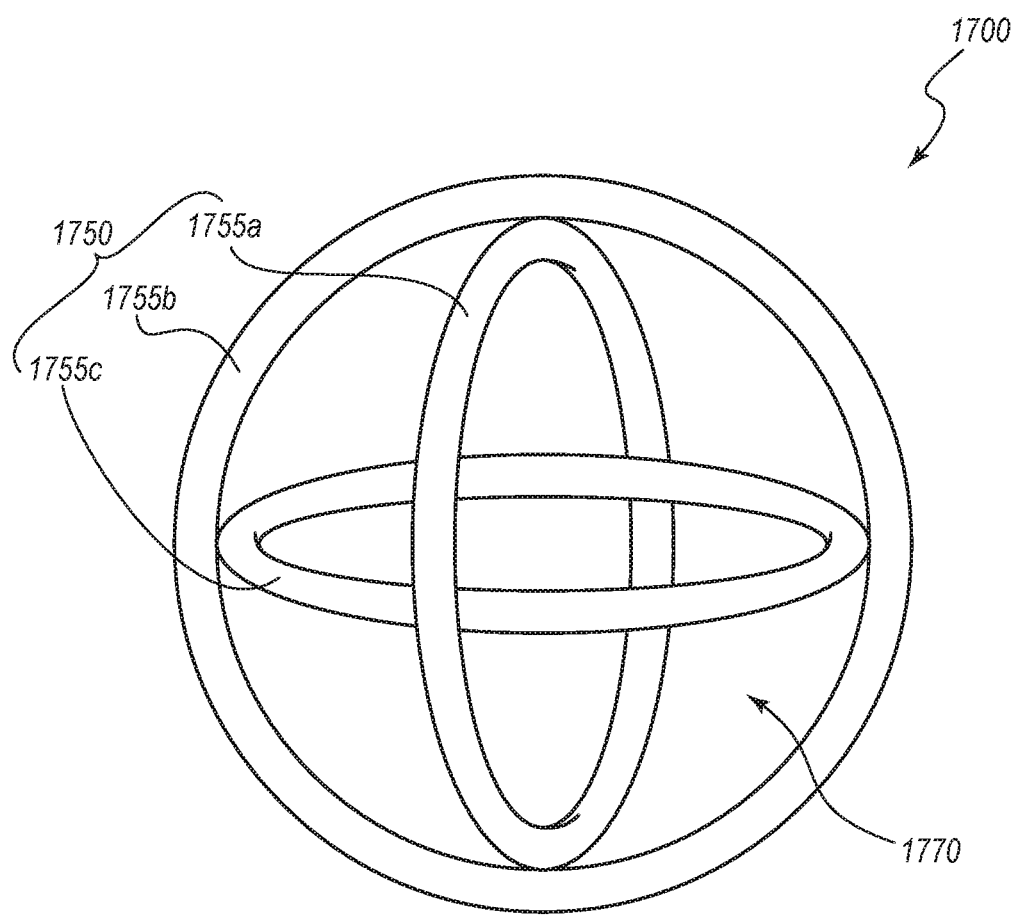
FIG. 17 is a perspective view of another embodiment of a medical device for the treatment of obesity.
Figure 18:
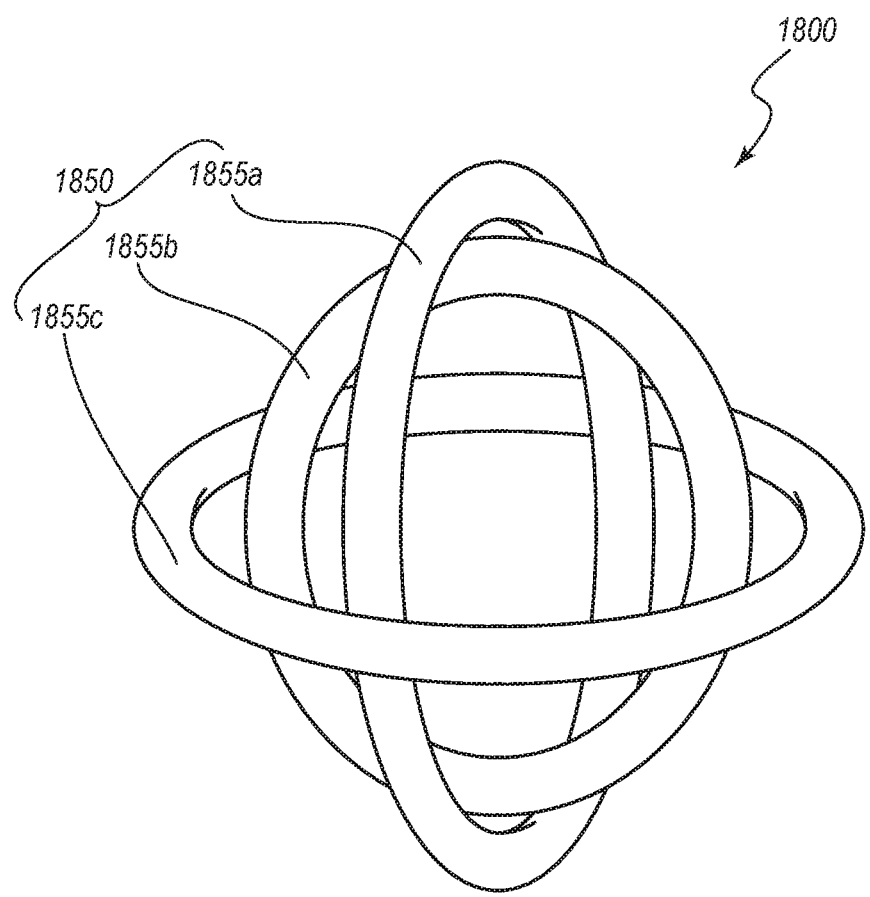
FIG. 18 is a perspective view of another embodiment of a medical device for the treatment of obesity.
Figure 19:
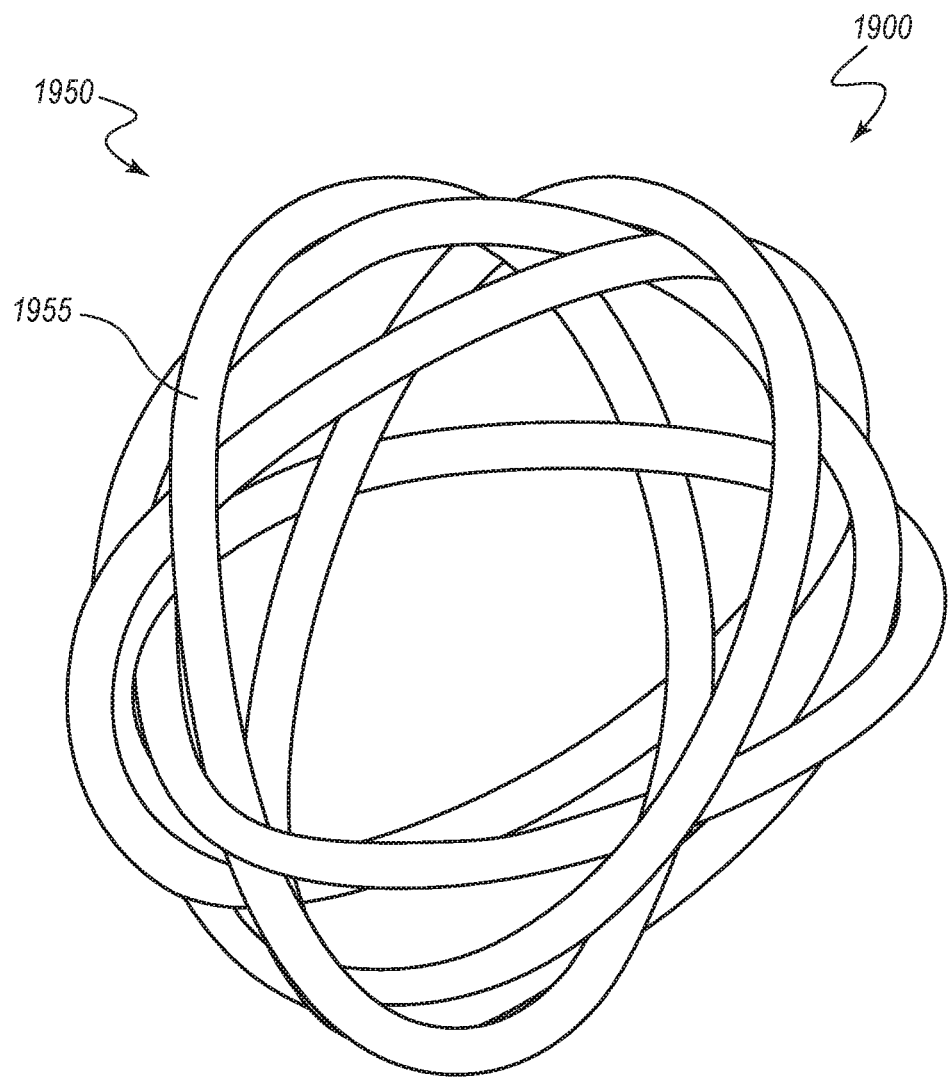
FIG. 19 is a perspective view of another embodiment of a medical device for the treatment of obesity.
Figure 20:
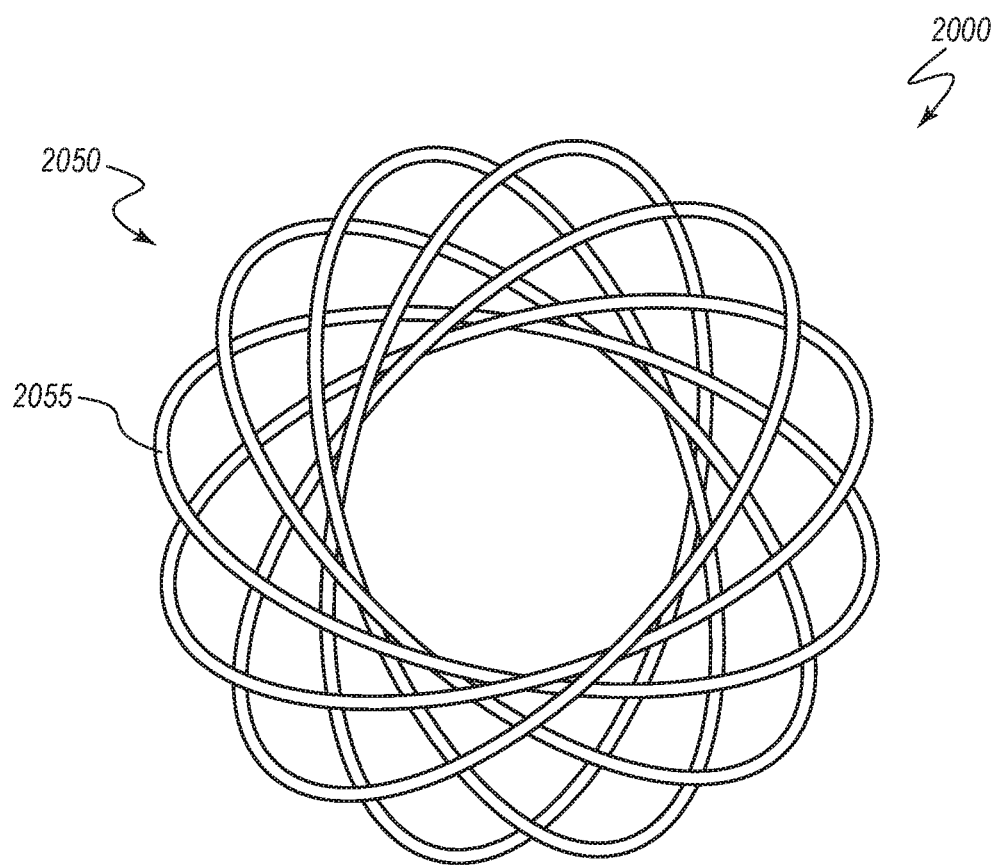
FIG. 20 is a front elevation view of another embodiment of a medical device for the treatment of obesity.

With reference to FIG. 17-20, inflatable or expandable structures can define a wide variety of configurations that may be capable of distending the bowel while permitting passage therethrough of material so as not to obstruct the lumen of the bowel. In FIG. 17, a device 1700 includes a body 1750 formed of three structures 1755a, 1755b, 1755c that are connected to one another at mutually perpendicular orientations. In FIG. 18, a device 1800 also includes a body 1850 formed of three structures 1855a, 1855b, 1855c that are connected to one another at mutually perpendicular orientations, but in a manner different from that of the device 1700. FIG. 19 depicts a device 1900 that includes a body 1850 formed of a single structure (e.g., a single inflatable balloon, rod, etc.) that forms a netted region substantially without symmetry. FIG. 20 depicts a device 2000 that includes a body 2050 formed of multiple structures (e.g., multiple inflatable balloons, rods, etc.) that form a netted region with multiple planes of symmetry.

In the event that various embodiments are not tolerated by a patient (e.g., cause excessive anorexia, nausea, and/or vomiting), the device may be removed in any suitable manner. For example, various embodiments ban be partially or completely removed by scraping, dissolving, deflating, collapsing, retracting, snaring, and/or any other suitable means.

In some embodiments disclosed herein, the implanted medical device may define a space-filling or volume-defining structure that may trigger an intestinal-gastric brake, but may only minimally or nominally distend the bowel wall, or may not distend the wall at all. For example, the device may merely fill the space (without causing partial or complete obstruction) and, potentially, may somewhat slow the flow of material. The presence of the device and/or its slowing of material could independently trigger an intestinal-gastric brake.

Figure 21:
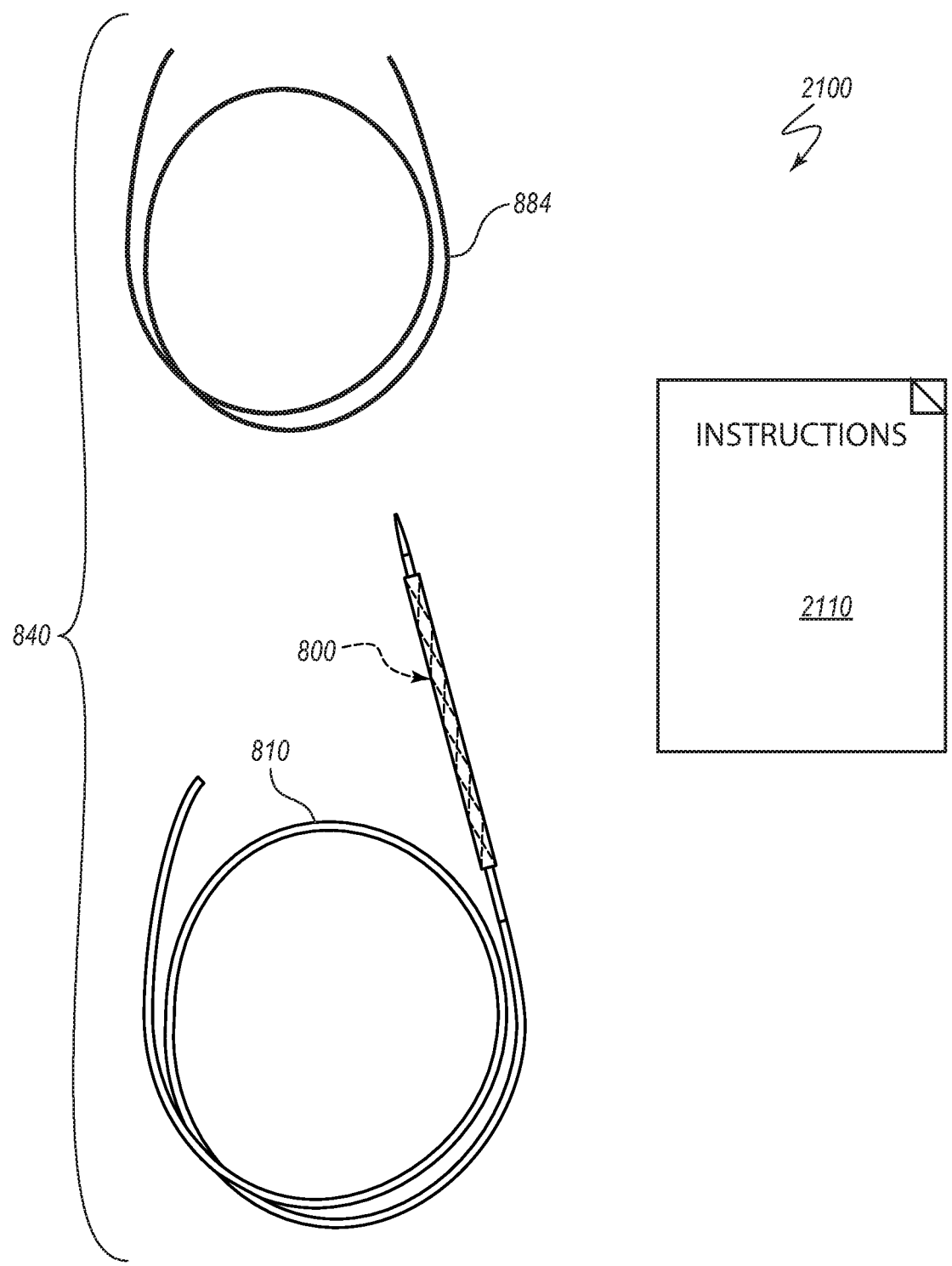
FIG. 21 is an elevation view of an embodiment of a kit for the treatment of obesity.

FIG. 21 depicts a kit 2100 that can be used in introducing a medical device into a patient. The kit 2100 can include any of the implantation systems disclosed herein and/or components thereof. For example, the kit 2100 can include any of the medical devices 300-2000 disclosed herein, along with any one or more of the systems or components thereof used to introduce the device into the patient and/or deploy the device.

In illustrated embodiment, the kit 2100 includes the system 840 described above, which includes a guidewire 884 and the medical device 800 coupled with the catheter 810. In other embodiments, the medical device 800 may be introduced via an endoscope (e.g., in manners previously discussed with respect to the system 840). In some embodiments, the kit 2100 may include an endoscope and/or accessories therefor, or may be specifically configured for use with a particular endoscope (e.g., colonoscope).

The kit 2100 can include instructions for use 2110, which may provide directions with respect to any of the processes disclosed herein. The instructions for use 2110 can specifically recommend or direct a user to deploy the medical kit within the bowel of the patient to distend the bowel for a clinically effective period. In various embodiments, the kit—and, in particular, the instructions for use thereof—can be approved of or authorized by a regulating body of a particular jurisdiction. For example, the kit, and the instructions for use thereof, may be approved of or authorized by the Food and Drug Administration of the United States of America and/or may comply with the regulations of other jurisdictions, such as by qualifying for CE marking in the European Union.

The claims that follow this written disclosure are expressly incorporated into the present written disclosure, with each claim standing on its own as a separate embodiment. In particular, each of the methods, kits, systems, and medical devices recited in the claims is expressly incorporated herein. Moreover, any of the methods described below may be used with any applicable system or medical device disclosed herein, as appropriate. Moreover, any of the kits disclosed above or disclosed in the claims can include instructions for carrying out any of the methods recited in the claims, as appropriate. This disclosure includes all permutations of the independent claims with their dependent claims.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. A method comprising:
   treating obesity of a patient by distending a portion of the bowel of the patient that comprises at least a portion of the cecum of the patient for an amount of time sufficient to reduce a total weight of the patient by no less than 5 percent,
   wherein distending the portion of the bowel comprises distending the cecum.

2. The method of claim 1, wherein the amount of time is sufficient to achieve a total weight loss of the patient of no less than 10 percent.

3. The method of claim 1, wherein the amount of time is sufficient to achieve an excess weight loss of the patient of no less than 10 percent.

4. The method of claim 1, wherein the amount of time is sufficient to achieve an excess weight loss of the patient of no less than 20 percent.

5. The method of claim 1, wherein the amount of time comprises no less than one month.

6. The method of claim 1, wherein the amount of time comprises no less than three months.

7. The method of claim 1, wherein the amount of time comprises no less than six months.

8. The method of claim 1, wherein distending the portion of the bowel reduces an appetite of the patient.

9. The method of claim 1, wherein distending the portion of the bowel triggers an intestinal-gastric brake in the patient.

10. The method of claim 1, further comprising distending the portion of the bowel without obstructing passage of material through the portion of the bowel.

11. The method of claim 1, further comprising reducing a flow capacity through a lumen defined by the portion of the bowel by no greater than 50 percent.

12. The method of claim 1, wherein distending the portion of the bowel comprises distending the portion of the bowel to an expanded configuration that is larger than a relaxed configuration of the portion of the bowel.

13. The method of claim 12, wherein the expanded configuration of the portion of the bowel is sufficiently large to trigger an intestinal-gastric brake in the patient.

14. The method of claim 1, wherein distending the portion of the bowel comprises contacting an inner surface of the portion of the bowel with an object that is of foreign origin relative to the body of the patient.

15. The method of claim 14, wherein the object comprises a natural object.

16. The method of claim 14, wherein the object comprises an artificial object.

17. The method of claim 14, wherein the object comprises a cage; a balloon; a stent; or a quantity of one or more of adhesive, fiber, cellulose, hemicellulose, lignan, mucilage, beta-glucan, pectin, guar, polydextrose, starch, dextrin, inulin, *psyllium*, or bran.

18. The method of claim 14, further comprising:
   advancing an endoscope into the patient toward the portion of the bowel; and
   introducing the object into the portion of the bowel via the endoscope.

19. The method of claim 18, wherein the object is coupled with a catheter, and wherein the method further comprises advancing the catheter along or substantially parallel to a longitudinal axis of the endoscope.

20. The method of claim 19, wherein said advancing the catheter along or substantially parallel to the longitudinal axis of the endoscope comprises advancing the catheter through a channel of the endoscope.

21. The method of claim 19, wherein said advancing the catheter along or substantially parallel to the longitudinal axis of the endoscope comprises advancing the catheter adjacent to an exterior surface of the endoscope.

22. The method of claim 14, further comprising securing the object to the inner surface of the portion of the bowel.

23. The method of claim 22, wherein securing the object comprises adhering the object to the inner surface of the portion of the bowel.

24. The method of claim 22, wherein securing the object comprises tensioning the object against the inner surface of the portion of the bowel.

25. The method of claim 22, wherein contacting the inner surface of the portion of the bowel with the object comprises contacting the bowel about a full periphery of the object.

26. The method of claim 14, wherein contacting the inner surface of the portion of the bowel with the object comprises contacting the bowel about a full periphery of the object.

27. The method of claim 14, wherein contacting the inner surface of the portion of the bowel with the object comprises contacting the inner surface about only a portion of a periphery of the object.

28. The method of claim 27, wherein said distending a portion of the bowel comprises distending only a portion of a full periphery of the portion of the bowel.

29. The method of claim 14, further comprising assembling the object within the bowel of the patient.

30. The method of claim 29, wherein said assembling the object comprises attaching separate components of the object to each other within the bowel.

31. The method of claim 30, wherein said attaching separate components of the object to each other comprises adhering the separate components to each other.

32. The method of claim 14, further comprising expanding the object within the portion of the bowel.

33. The method of claim 32, wherein the object is self-expanding, the method further comprising permitting the object to self-expand within the portion of the bowel.

34. The method of claim 32, wherein said expanding the object comprises inflating the object.

35. The method of claim 32, wherein said expanding the object comprises inflating a balloon positioned at an interior of the object.

36. The method of claim 32, wherein said expanding the object comprises reorienting separate components of the object.

37. The method of claim 14, wherein the object comprises a medical device.

38. The method of claim 37, wherein the medical device comprises a body and a wall of the bowel comprises the inner surface of the portion of the bowel, and wherein the method further comprises contacting the wall of the bowel with the body of the medical device to distend the bowel.

39. The method of claim 37, wherein a wall of the bowel comprises the inner surface of the portion of the bowel, and wherein the method further comprises securing the medical device to the wall of the bowel.

40. The method of claim 39, wherein said securing comprises tensioning the medical device against the wall of the bowel.

41. The method of claim 37, wherein the medical device is configured to transition from an undeployed state to an expanded state, the method further comprising transitioning the medical device from the undeployed state to the expanded state within the portion of the bowel.

42. The method of claim 41, further comprising passing the medical device through a region of the bowel that is adjacent to the portion of the bowel while the medical device is in the undeployed state.

43. The method of claim 42, further comprising advancing a guidewire through the colon toward the portion of the bowel, wherein said passing the medical device through the region of the bowel that is adjacent to the portion of the bowel while the medical device is in the undeployed state comprises advancing the medical device along the guidewire.

44. The method of claim 43, wherein the medical device is coupled with a catheter, and wherein said passing the medical device through the region of the bowel that is adjacent to the portion of the bowel comprises advancing the catheter over the guidewire.

45. The method of claim 41, further comprising introducing the medical device into the patient through the rectum of the patient while the medical device is in the undeployed state.

46. The method of claim 41, further comprising:
   advancing an endoscope into the patient toward the portion of the bowel; and
   introducing the medical device into the portion of the bowel via the endoscope.

47. The method of claim 46, wherein said introducing the medical device into the portion of the bowel via the endoscope comprises advancing the medical device through or alongside the endoscope while the medical device is in the undeployed state.

48. The method of claim 46, wherein said introducing the medical device into the portion of the bowel via the endoscope comprises passing the medical device along or substantially parallel to a longitudinal axis of the endoscope while the medical device is in the undeployed state.

49. The method of claim 48, wherein said passing the medical device along or substantially parallel to the longitudinal axis of the endoscope comprises passing the medical device through a channel of the endoscope.

50. The method of claim 48, wherein said passing the medical device along or substantially parallel to the longitudinal axis of the endoscope comprises advancing the medical device adjacent to an exterior surface of the endoscope.

51. The method of claim 48, wherein the medical device is coupled to a catheter, and wherein said passing the medical device along or substantially parallel to the longitudinal axis of the endoscope comprises passing the catheter along or substantially parallel to the longitudinal axis of the endoscope.

52. The method of claim 51, further comprising expanding the medical device into contact with the inner surface of the portion of the bowel via the catheter.

53. The method of claim 52, wherein said expanding the medical device comprises inflating a balloon that is coupled to the catheter and positioned at an interior of the medical device.

54. The method of claim 52, wherein the medical device comprises a stent.

55. The method of claim 52, wherein said expanding the medical device comprises inflating the medical device.

56. The method of claim 55, wherein said inflating comprises:
passing fluid through the catheter; and
introducing the fluid into the medical device.

57. The method of claim 55, wherein the medical device comprises a balloon.

58. The method of claim 41, wherein the medical device is coupled with a catheter in the undeployed state, wherein the method further comprises advancing the catheter into the patient toward the portion of the bowel, and wherein said transitioning the medical device from the undeployed state to the expanded state is achieved via the catheter.

59. The method of claim 58, wherein said transitioning the medical device comprises moving an expansion element relative to the catheter to expand the medical device.

60. The method of claim 59, wherein the expansion element comprises a fluid for inflating a balloon that is coupled to the catheter at a position internal to the medical device, and wherein said moving the expansion element comprises passing the fluid through the catheter and into the balloon to expand the balloon.

61. The method of claim 59, wherein the expansion element comprises a fluid for inflating the medical device, and wherein said moving the expansion element comprises passing the fluid through the catheter into the medical device.

62. The method of claim 59, wherein the expansion element comprises a restrictive sleeve, and wherein said moving the expansion element comprises removing the restrictive sleeve from the medical device to permit the medical device to self-expand.

63. The method of claim 59, wherein the expansion element comprises an actuation wire coupled to the medical device.

64. The method of claim 41, wherein the medical device is coupled with an endoscope in the undeployed state, wherein the method further comprises advancing the endoscope into the patient toward the portion of the bowel, and wherein said transitioning the medical device from the undeployed state to the expanded state is achieved via the endoscope.

65. The method of claim 64, wherein said transitioning the medical device comprises moving an expansion element relative to the endoscope.

66. The method of claim 65, wherein the expansion element comprises a fluid for inflating the medical device, and wherein said moving the expansion element comprises passing the fluid through or alongside the endoscope.

67. The method of claim 66, wherein the endoscope defines a channel, and wherein said passing the fluid through or alongside the endoscope comprises passing the fluid through the channel.

68. The method of claim 66, wherein a removable covering that defines a lumen is coupled to the endoscope, and wherein said passing the fluid through or alongside the endoscope comprises passing the fluid through the lumen of the covering.

69. The method of claim 65, wherein the expansion element comprises a restrictive sleeve, and wherein said moving the expansion element comprises removing the restrictive sleeve from the medical device to permit the medical device to expand.

70. The method of claim 65, wherein the expansion element comprises an actuation wire coupled to the medical device.

71. The method of claim 41, wherein the medical device defines at least a portion of a passageway when in the expanded state, the method further comprising permitting material to pass through the passageway.

72. The method of claim 71, wherein the medical device comprises one or more of a plurality of openings in fluid communication with the passageway.

73. The method of claim 71, wherein the material that passes through the passageway comprises material that, in the absence of the medical device, would naturally pass through the portion of the bowel.

74. The method of claim 71, wherein the material that passes through the passageway comprises one or more of gas, semi-liquid, liquid, semi-solid, and solid material that naturally passes through the bowel.

75. The method of claim 41, wherein the medical device comprises an expandable frame.

76. The method of claim 75, wherein the expandable frame comprises a shape memory material.

77. The method of claim 41, wherein the medical device comprises a stent.

78. The method of claim 41, wherein the medical device comprises a cage.

79. The method of claim 41, wherein the medical device comprises a balloon.

80. The method of claim 41, wherein said transitioning the medical device from the undeployed state to the expanded state within the portion of the bowel comprises bringing the medical device into contact with the inner surface of the portion of the bowel.

81. The method of claim 80, further comprising transitioning the medical device from the expanded state to the undeployed state after the amount of time sufficient to reduce the total weight of the patient by no less than 5 percent has passed.

82. The method of claim 81, further comprising, after said transitioning the medical device from the expanded state to the undeployed state, removing the medical device from the patient while the medical device is in the undeployed state.

83. The method of claim 82, wherein said removing the medical device from the patient is achieved by passing the medical device through a channel of an endoscope.

84. The method of claim 41, further comprising removing the medical device from the patient after the amount of time sufficient to reduce the total weight of the patient by no less than 5 percent has passed.

85. The method of claim 37, wherein the medical device comprises a bioresorbable material.

86. The method of claim 85, further comprising permitting the bioresorbable material to naturally degrade within the patient until the medical device no longer contacts the inner surface of the portion of the bowel.

87. The method of claim 86, further comprising passing the medical device through the bowel and out of the patient after said permitting the bioresorbable material to naturally degrade.

88. The method of claim 86, wherein said permitting the bioresorbable material to naturally degrade occurs for a period of no less than one month.

89. The method of claim 86, wherein the medical device exhibits sufficient structural rigidity to tension the medical device against the inner surface of the portion of the bowel to achieve distention of the portion of the bowel prior to degradation of the bioresorbable material, and wherein the structural rigidity of the medical device is reduced as the bioresorbable material naturally degrades.

90. The method of claim 89, further comprising permitting the medical device to cease distention of the portion of the bowel upon sufficient degradation of the bioresorbable material.

91. The method of claim 90, further comprising passing the medical device through the bowel and out of the patient after said ceasing distention of the portion of the bowel.

92. The method of claim 90, wherein the medical device comprises a cage, a stent, or a balloon.

93. The method of claim 85, wherein the medical device comprises a balloon that comprises the bioresorbable material, the method further comprising permitting the bioresorbable material to naturally degrade within the patient until the balloon at least partially deflates.

94. The method of claim 93, wherein a wall of the balloon comprises the bioresorbable material, and wherein natural degradation of the bioresorbable material causes the wall to leak fluid from an interior of the balloon.

95. The method of claim 93, wherein a closure of the balloon comprises the bioresorbable material, and wherein natural degradation of the bioresorbable material causes fluid to leak from the balloon.

96. The method of claim 95, wherein the closure comprises a one-way valve.

97. The method of claim 93, further comprising passing the balloon through the bowel of the patient after the balloon at least partially deflates.

98. The method of claim 85, the method further comprising permitting the bioresorbable material to naturally degrade within the patient such that the medical device is broken down into a plurality of separate pieces.

99. The method of claim 98, further comprising passing each of the separate pieces through the bowel.

100. The method of claim 98, wherein the bioresorbable material holds together the separate pieces prior to degradation, and wherein degradation of the bioresorbable material releases the separate pieces from each other.

101. The method of claim 37, wherein the medical device comprises an eluting material, the method further comprising permitting the eluting material of the medical device to release one or more appetite suppressants.

102. The method of claim 101, wherein the one or more appetite suppressants are selected from the group consisting of: one or more drugs, one or more nutrients, one or more hormones, one or more peptides, one or more neurotransmitters, one or more bacteria, and combinations thereof.

103. The method of claim 37, wherein the medical device is positioned solely in the cecum.

104. The method of claim 1, wherein said distending the portion of the bowel comprises intermittently distending the portion of the bowel.

105. The method of claim 104, wherein said intermittently distending the portion of the bowel comprises alternatingly distending the portion of the bowel and refraining from distending the portion of the bowel.

106. The method of claim 1, wherein said distending the portion of the bowel comprises partially distending the portion of the bowel.

107. The method of claim 106, wherein said partially distending the portion of the bowel comprises distending the portion of the bowel around only a portion of a full periphery thereof.

108. The method of claim 107, wherein said partially distending the portion of the bowel is achieved via a medical device.

109. The method of claim 108, wherein the medical device freely floats within the bowel.

110. The method of claim 1, wherein distending the portion of the bowel comprises distending only the cecum.

111. A method comprising:
treating obesity of a patient by distending a portion of the bowel of the patient that comprises at least a portion of the cecum of the patient for an amount of time sufficient to reduce an excess weight of the patient by no less than 10 percent, wherein the excess weight is calculated as a difference between an actual body weight of the patient and a weight necessary to achieve a body mass index of 24.9 for the patient, and
wherein distending the portion of the bowel comprises distending the cecum.

112. The method of claim 111, wherein distending the portion of the bowel comprises contacting an inner surface of the portion of the bowel with a medical device.

113. The method of claim 112, wherein a wall of the bowel comprises the inner surface of the portion of the bowel, and wherein the method further comprises securing the medical device to the wall of the bowel.

114. The method of claim 113, wherein said securing comprises tensioning the medical device against the wall of the bowel.

115. The method of claim 112, wherein the medical device is configured to transition from an undeployed state to an expanded state, the method further comprising transitioning the medical device from the undeployed state to the expanded state within the portion of the bowel.

116. The method of claim 115, further comprising:
advancing an endoscope into the patient toward the portion of the bowel; and
introducing the medical device into the portion of the bowel via the endoscope.

117. The method of claim 116, further comprising advancing the medical device through or alongside the endoscope while the medical device is in the undeployed state.

118. A method comprising:
treating obesity of a patient by distending a portion of the bowel of the patient that comprises at least a portion of the cecum of the patient for a period of no less than one month,
wherein distending the portion of the bowel comprises distending the cecum.

119. The method of claim 118, wherein distending the portion of the bowel comprises contacting an inner surface of the portion of the bowel with a medical device.

120. The method of claim 119, wherein a wall of the bowel comprises the inner surface of the portion of the bowel, and wherein the method further comprises securing the medical device to the wall of the bowel.

121. The method of claim 120, wherein said securing comprises tensioning the medical device against the wall of the bowel.

122. The method of claim 119, wherein the medical device is configured to transition from an undeployed state to an expanded state, the method further comprising transitioning the medical device from the undeployed state to the expanded state within the portion of the bowel.

123. The method of claim 122, further comprising:
advancing an endoscope into the patient toward the portion of the bowel; and introducing the medical device into the portion of the bowel via the endoscope.

124. The method of claim 123, further comprising advancing the medical device through or alongside the endoscope while the medical device is in the undeployed state.

125. A method comprising:
introducing a medical device into the cecum of an obese patient;
distending the cecum via the medical device to reduce an appetite of the patient; and
leaving the medical device within the cecum while the medical device maintains the cecum in distention.

126. The method of claim 125, wherein said leaving the medical device within the cecum while the medical device maintains the cecum in distention takes place for an amount of time sufficient to reduce a total weight of the patient by no less than 5 percent.

127. The method of claim 125, wherein said leaving the medical device within the cecum while the medical device maintains the cecum in distention takes place for an amount of time sufficient to achieve a total weight loss of the patient of no less than 10 percent.

128. The method of claim 125, wherein said leaving the medical device within the cecum while the medical device maintains the cecum in distention takes place for an amount of time sufficient to achieve an excess weight loss of the patient of no less than 10 percent.

129. The method of claim 125, wherein said leaving the medical device within the cecum while the medical device maintains the cecum in distention takes place for an amount of time sufficient to achieve an excess weight loss of the patient of no less than 20 percent.

130. The method of claim 125, wherein said leaving the medical device within the cecum while the medical device maintains the cecum in distention takes place for no less than one month.

131. The method of claim 125, wherein said leaving the medical device within the cecum while the medical device maintains the cecum in distention takes place for no less than three months.

132. The method of claim 125, wherein said leaving the medical device within the cecum while the medical device maintains the cecum in distention takes place for no less than six months.

133. The method of claim 125, wherein distending the cecum of the patient triggers an intestinal-gastric brake in the patient.

134. The method of claim 125, further comprising distending the cecum via the medical device without the medical device obstructing passage of material through the cecum.

135. The method of claim 125, further comprising reducing a flow capacity through a lumen defined by the cecum by no greater than 50 percent.

136. The method of claim 125, wherein distending the cecum comprises distending the cecum to an expanded configuration that is larger than a relaxed configuration of the cecum.

137. The method of claim 136, wherein the expanded configuration of the cecum is sufficiently large to trigger an intestinal-gastric brake in the patient.

138. The method of claim 125, wherein the medical device comprises a body, and wherein the method further comprises contacting a wall of the cecum with the body of the medical device to distend the cecum.

139. The method of claim 138, further comprising securing the medical device to the wall of the cecum.

140. The method of claim 139, wherein said securing comprises tensioning the medical device against the wall of the cecum.

141. The method of claim 125, wherein the medical device is configured to transition from an undeployed state to an expanded state, the method further comprising transitioning the medical device from the undeployed state to the expanded state within the cecum.

142. The method of claim 141, further comprising passing the medical device through a region of the bowel that is adjacent to the cecum while the medical device is in the undeployed state.

143. The method of claim 142, further comprising advancing a guidewire through the colon toward the cecum, wherein said passing the medical device through a region of the bowel that is adjacent to the cecum while the medical device is in the undeployed state comprises advancing the medical device along the guidewire.

144. The method of claim 143, wherein the medical device is coupled with a catheter, and wherein said passing the medical device through the region of the bowel that is adjacent to the cecum comprises advancing the catheter over the guidewire.

145. The method of claim 141, further comprising introducing the medical device into the patient through the rectum of the patient while the medical device is in the undeployed state.

146. The method of claim 141, further comprising:
advancing an endoscope into the patient toward the cecum; and
introducing, via the endoscope, the medical device into the cecum.

147. The method of claim 146, wherein said introducing, via the endoscope, the medical device into the cecum comprises advancing the medical device through or alongside the endoscope while the medical device is in the undeployed state.

148. The method of claim 147, wherein said transitioning the medical device from the undeployed state to the expanded state within the cecum comprises bringing the medical device into contact with an inner surface of the cecum.

149. The method of claim 146, wherein said introducing, via the endoscope, the medical device into the cecum comprises passing the medical device along or substantially parallel to a longitudinal axis of the endoscope.

150. The method of claim 149, wherein said passing the medical device along or substantially parallel to the longitudinal axis of the endoscope comprises passing the medical device through a channel of the endoscope.

151. The method of claim 149, wherein said passing the medical device along or substantially parallel to the longitudinal axis of the endoscope comprises passing the medical device adjacent to an exterior surface of the endoscope.

152. The method of claim 149, wherein the medical device is coupled to a catheter, and wherein said passing the medical device along or substantially parallel to the longitudinal axis of the endoscope comprises passing the catheter along or substantially parallel to the longitudinal axis of the endoscope.

153. The method of claim 152, further comprising expanding the medical device into contact with a wall of the cecum via the catheter.

154. The method of claim 153, wherein said expanding the medical device comprises inflating a balloon that is coupled to the catheter and positioned at an interior of the medical device.

155. The method of claim 153, wherein the medical device comprises a stent.

156. The method of claim 155, wherein the stent is self-expanding.

157. The method of claim 153, wherein said expanding the medical device comprises inflating the medical device.

158. The method of claim 157, wherein said inflating comprises:
passing fluid through the catheter; and
introducing the fluid into the medical device.

159. The method of claim 157, wherein the medical device comprises a balloon.

160. The method of claim 141, wherein the medical device is coupled with a catheter in the undeployed state, wherein the method further comprises advancing the catheter into the patient toward the cecum, and wherein said transitioning the medical device from the undeployed state to the expanded state is achieved via the catheter.

161. The method of claim 160, wherein said transitioning the medical device comprises moving an expansion element relative to the catheter to expand the medical device.

162. The method of claim 161, wherein the expansion element comprises a fluid for inflating a balloon that is coupled to the catheter at a position internal to the medical device, and wherein said moving the expansion element comprises passing the fluid through the catheter and into the balloon to expand the balloon.

163. The method of claim 161, wherein the expansion element comprises a fluid for inflating the medical device, and wherein said moving the expansion element comprises passing the fluid through the catheter into the medical device.

164. The method of claim 161, wherein the expansion element comprises a restrictive sleeve, and wherein said moving the expansion element comprises removing the restrictive sleeve from the medical device to permit the medical device to self-expand.

165. The method of claim 161, wherein the expansion element comprises an actuation wire coupled to the medical device.

166. The method of claim 141, wherein the medical device is coupled with an endoscope in the undeployed state, wherein the method further comprises advancing the endoscope into the patient toward the cecum, and wherein said transitioning the medical device from the undeployed state to the expanded state is achieved via the endoscope.

167. The method of claim 166, wherein said transitioning the medical device from the undeployed state to the expanded state comprises moving an expansion element relative to the endoscope.

168. The method of claim 167, wherein the expansion element comprises a fluid for inflating the medical device, and wherein said moving the expansion element comprises passing the fluid through or alongside the endoscope.

169. The method of claim 168, wherein a removable covering that defines a lumen is coupled to the endoscope, and wherein said passing the fluid through or alongside the endoscope comprises passing the fluid through the lumen.

170. The method of claim 168, wherein the endoscope defines a channel, and wherein said passing the fluid through the endoscope comprises passing the fluid through the channel.

171. The method of claim 167, wherein the expansion element comprises a restrictive sleeve, and wherein said moving the expansion element comprises removing the restrictive sleeve from the medical device to permit the medical device to expand.

172. The method of claim 167, wherein the expansion element comprises an actuation wire coupled to the medical device.

173. The method of claim 141, wherein the medical device defines at least a portion of a passageway when in the expanded state, the method further comprising permitting material to pass through the passageway.

174. The method of claim 173, wherein the material that passes through the passageway comprises material that, in the absence of the medical device, would naturally pass through the cecum.

175. The method of claim 173, wherein the material that passes through the passageway comprises one or more of gas, semi-liquid, liquid, semi-solid, and solid material that naturally passes through the cecum.

176. The method of claim 141, wherein the medical device comprises an expandable frame.

177. The method of claim 176, wherein the expandable frame comprises a shape memory material.

178. The method of claim 141, wherein the medical device comprises a stent.

179. The method of claim 141, wherein the medical device comprises a cage.

180. The method of claim 141, wherein the medical device comprises a balloon.

181. The method of claim 141, further comprising transitioning the medical device from the undeployed state to the expanded state into contact with a wall of the cecum.

182. The method of claim 125, wherein the medical device comprises a bioresorbable material.

183. The method of claim 182, further comprising permitting the bioresorbable material to naturally degrade within the patient.

184. The method of claim 183, further comprising passing the medical device through the bowel of the patient and out of the patient after said permitting the bioresorbable material to naturally degrade.

185. The method of claim 182, wherein the medical device exhibits sufficient structural rigidity to tension the medical device against an inner surface of the cecum to achieve distention of the cecum, and wherein the structural rigidity of the medical device is reduced as the bioresorbable material naturally degrades.

186. The method of claim 185, further comprising permitting the medical device to cease distention of the cecum upon sufficient degradation of the bioresorbable material.

187. The method of claim 125, further comprising removing the medical device from the patient.

188. The method of claim 125, wherein the medical device comprises an eluting material, the method further comprising permitting the eluting material of the medical device to release one or more appetite suppressants.

189. The method of claim 188, wherein the one or more appetite suppressants are selected from the group consisting of: one or more drugs, one or more nutrients, one or more hormones, one or more peptides, one or more neurotransmitters, one or more bacteria, and combinations thereof.

190. A method comprising:
treating obesity of a patient by distending the cecum of the patient for an amount of time sufficient to reduce a total weight of the patient by no less than 5 percent, wherein distending the cecum comprises placing a medical device in contact with an inner surface of the cecum, and wherein the medical device comprises an eluting material, the method further comprising permitting the eluting material of the medical device to release one or more appetite suppressants.

191. The method of claim 190, wherein the one or more appetite suppressants are selected from the group consisting of: one or more drugs, one or more nutrients, one or more hormones, one or more peptides, one or more neurotransmitters, one or more bacteria, and combinations thereof.

192. A method comprising:

treating obesity of a patient by distending the cecum of the patient for an amount of time sufficient to reduce an excess weight of the patient by no less than 10 percent, wherein the excess weight is calculated as a difference between an actual body weight of the patient and a weight necessary to achieve a body mass index of 24.9 for the patient, wherein distending the cecum comprises placing a medical device in contact with an inner surface of the cecum, and wherein the medical device comprises an eluting material, the method further comprising permitting the eluting material of the medical device to release one or more appetite suppressants.

193. The method of claim 192, wherein the one or more appetite suppressants are selected from the group consisting of: one or more drugs, one or more nutrients, one or more hormones, one or more peptides, one or more neurotransmitters, one or more bacteria, and combinations thereof.

194. A method comprising:

treating obesity of a patient by distending the cecum of the patient for a period of no less than one month, wherein distending the cecum comprises placing a medical device in contact with an inner surface of the cecum, and wherein the medical device comprises an eluting material, the method further comprising permitting the eluting material of the medical device to release one or more appetite suppressants.

195. The method of claim 194, wherein the one or more appetite suppressants are selected from the group consisting of: one or more drugs, one or more nutrients, one or more hormones, one or more peptides, one or more neurotransmitters, one or more bacteria, and combinations thereof.

* * * * *